US010426588B2

(12) United States Patent
Lam et al.

(10) Patent No.: US 10,426,588 B2
(45) Date of Patent: Oct. 1, 2019

(54) CONTAINER, APPARATUS AND METHOD FOR HANDLING AN IMPLANT

(71) Applicant: NOVA PLASMA LTD., Megiddo (IL)

(72) Inventors: Amnon Lam, Kibbutz Givat Oz (IL); Aviad Harhol, Tel Aviv (IL); Eliezer Fuchs, Kibbutz Megido (IL); Chen Porat, Kiryat Tivon (IL)

(73) Assignee: NOVA PLASMA LTD., Megiddo (IL)

( * ) Notice: Subject to any disclaimer, the term of this patent is extended or adjusted under 35 U.S.C. 154(b) by 643 days.

(21) Appl. No.: 15/101,684

(22) PCT Filed: Dec. 10, 2014

(86) PCT No.: PCT/IL2014/051079
§ 371 (c)(1),
(2) Date: Jun. 3, 2016

(87) PCT Pub. No.: WO2015/087326
PCT Pub. Date: Jun. 18, 2015

(65) Prior Publication Data
US 2016/0302906 A1 Oct. 20, 2016

Related U.S. Application Data

(60) Provisional application No. 62/053,815, filed on Sep. 23, 2014, provisional application No. 62/011,086, (Continued)

(51) Int. Cl.
*A61F 2/00* (2006.01)
*A01N 1/02* (2006.01)
(Continued)

(52) U.S. Cl.
CPC .......... *A61F 2/0095* (2013.01); *A01N 1/0263* (2013.01); *A01N 1/0273* (2013.01);
(Continued)

(58) Field of Classification Search
CPC .......... A61C 19/02; A61F 2/02; A61F 2/0095; A01N 1/0273; A01N 1/0294
See application file for complete search history.

(56) References Cited

U.S. PATENT DOCUMENTS 3,851,436 A  12/1974 Fraser
4,846,101 A  7/1989 Montgomery
(Continued)

FOREIGN PATENT DOCUMENTS

CN  101711708 A  5/2010
JP  2008-515616 A  5/2008
(Continued)

OTHER PUBLICATIONS

Duske et al., (2012) Atmospheric plasma enhances wettability and cell spreading on dental implant metals. J Clin Periodontol 39(4): 400-7.
(Continued)

*Primary Examiner* — Cachet I Proctor
(74) *Attorney, Agent, or Firm* — Dorsey & Whitney LLP

(57) ABSTRACT

A portable container is provided for handling an implant. The portable container comprises a sealed compartment enclosing a fluid of a pre-defined composition and at least one implant configured to be installed in a live subject. The portable container may further comprise at least one electrode made of an electrical conductive material, electrically associated with an electric conductor outside the sealed compartment and configured for applying a plasma generating electric field inside the sealed compartment. An apparatus for plasma treatment of an implant and having an activation device is further provided. The activation device comprises a slot configured to receive a portable container, and an electrical circuit configured to be electrically associated with at least one electrode. The electrical circuit is configured to provide to the at least one electrode electric (Continued)

power suitable for applying a plasma generating electric field in the sealed compartment, when the portable container is disposed in the slot.

28 Claims, 12 Drawing Sheets

Related U.S. Application Data filed on Jun. 12, 2014, provisional application No. 61/913,943, filed on Dec. 10, 2013.

(51) Int. Cl.

| | | |
|---|---|---|
| *A61F 2/12* | (2006.01) | |
| *A61L 2/14* | (2006.01) | |
| *A61L 27/04* | (2006.01) | |
| *A61L 27/12* | (2006.01) | |
| *A61L 27/24* | (2006.01) | |
| *H01J 37/32* | (2006.01) | |

(52) U.S. Cl.
CPC .............. *A01N 1/0294* (2013.01); *A61F 2/12* (2013.01); *A61L 2/14* (2013.01); *A61L 27/04* (2013.01); *A61L 27/12* (2013.01); *A61L 27/24* (2013.01); *H01J 37/32045* (2013.01); *H01J 37/32366* (2013.01); *H01J 37/32513* (2013.01); *H01J 37/32825* (2013.01); *A61F 2250/0043* (2013.01); *A61L 2400/18* (2013.01); *H01J 2237/327* (2013.01); *H01J 2237/335* (2013.01)

(56) References Cited

U.S. PATENT DOCUMENTS

| | | | | |
|---|---|---|---|---|
| 4,955,901 | A | 9/1990 | Nishiguchi | |
| 5,558,230 | A * | 9/1996 | Fischer | A61C 8/0087 206/570 |
| 5,697,997 | A | 12/1997 | Aronsson | |
| 5,960,956 | A * | 10/1999 | Langanki | A01N 1/02 206/364 |
| 7,451,870 | B2 * | 11/2008 | Donahoe | A61C 8/0087 206/369 |
| 8,071,042 | B2 | 12/2011 | Kuhry | |
| 8,518,420 | B2 | 8/2013 | Biris | |
| 2004/0037946 | A1 | 2/2004 | Morra | |
| 2005/0035015 | A1 * | 2/2005 | Bressler | A61C 8/0087 206/368 |
| 2007/0084144 | A1 * | 4/2007 | Labrecque | A61L 2/07 53/425 |
| 2007/0225785 | A1 | 9/2007 | Park | |
| 2009/0192528 | A1 | 7/2009 | Higgins | |
| 2010/0047532 | A1 | 2/2010 | Mozetic | |
| 2011/0095688 | A1 | 4/2011 | Bisges | |
| 2012/0183437 | A1 | 7/2012 | Keener | |
| 2013/0230426 | A1 * | 9/2013 | Popot | A61L 2/14 422/29 |
| 2014/0224687 | A1 * | 8/2014 | Schuster | A61L 2/26 206/363 |
| 2014/0377320 | A1 | 12/2014 | Pietramaggiori | |
| 2016/0000052 | A1 * | 1/2016 | Lin | A01K 63/04 210/345 |
| 2016/0264274 | A1 * | 9/2016 | Kulaga | B65B 55/12 |

FOREIGN PATENT DOCUMENTS

| | | |
|---|---|---|
| WO | 9312821 | 7/1993 |
| WO | 00/14146 A1 | 3/2000 |
| WO | 2007103705 | 9/2007 |
| WO | 2013056844 | 4/2013 |
| WO | 2015/091104 A1 | 6/2015 |
| WO | 2015083155 | 6/2015 |
| WO | 2016181396 | 11/2016 |

OTHER PUBLICATIONS

Heinlin et al., (2010) Plasma medicine: possible applications in dermatology. J Dtsch Dermatol Ges 8(12): 968-76.

Lee et al., (2011) Improvement of Hydrophilicity of Interconnected Porous Hydroxyapatite by Dielectric Barrier Discharge Plasma Treatment. IEEE Transactions on Plasma Science 39(11): 2166-2167.

Moriguchi et al., (2012) Plasma Surface Modification of Artificial Bones for Bone Regeneration. 4th International Conference on Plasma Medicine (ICPM 4); Jun. 17-21, 2012 Orleans, France. Abstract.

* cited by examiner

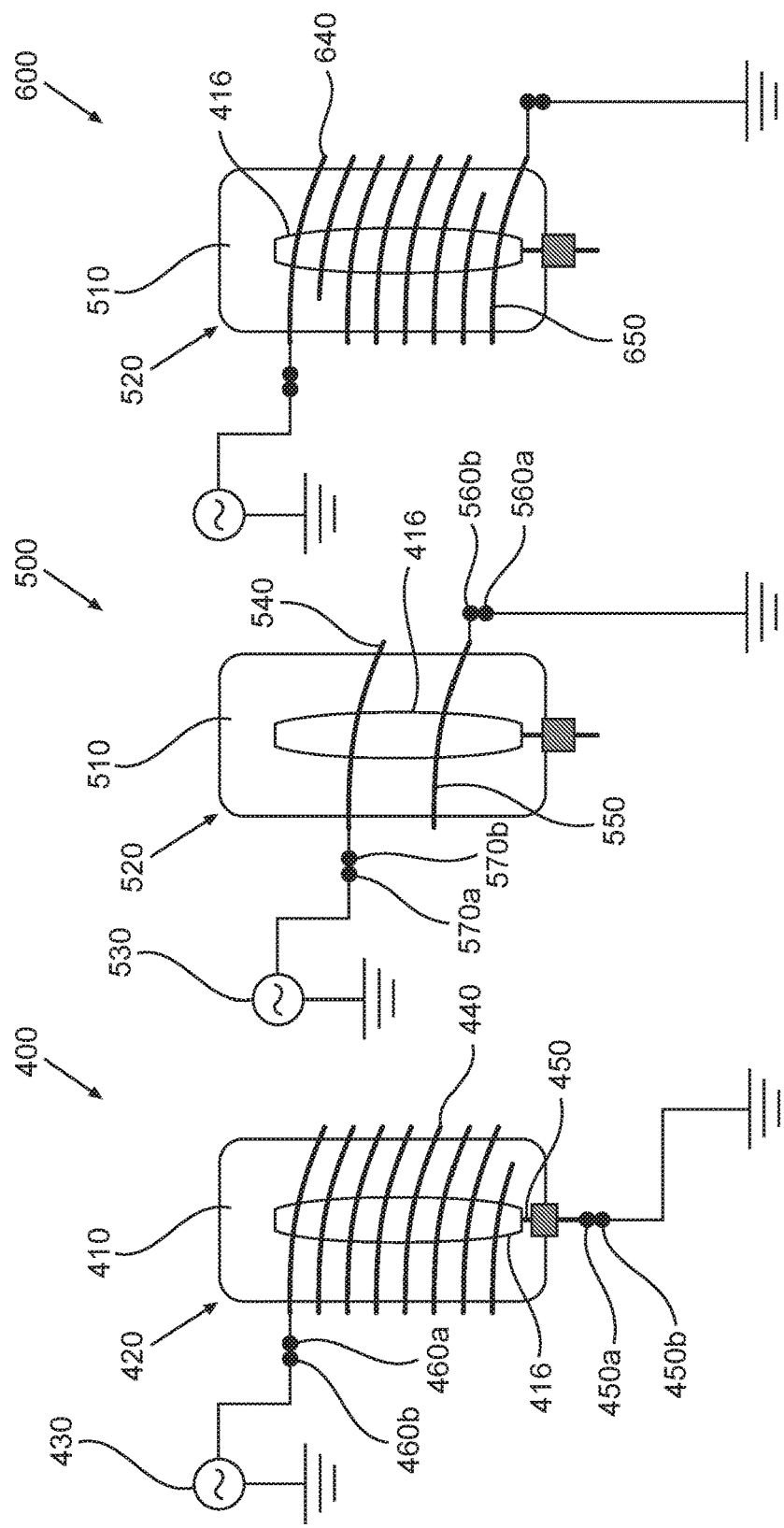

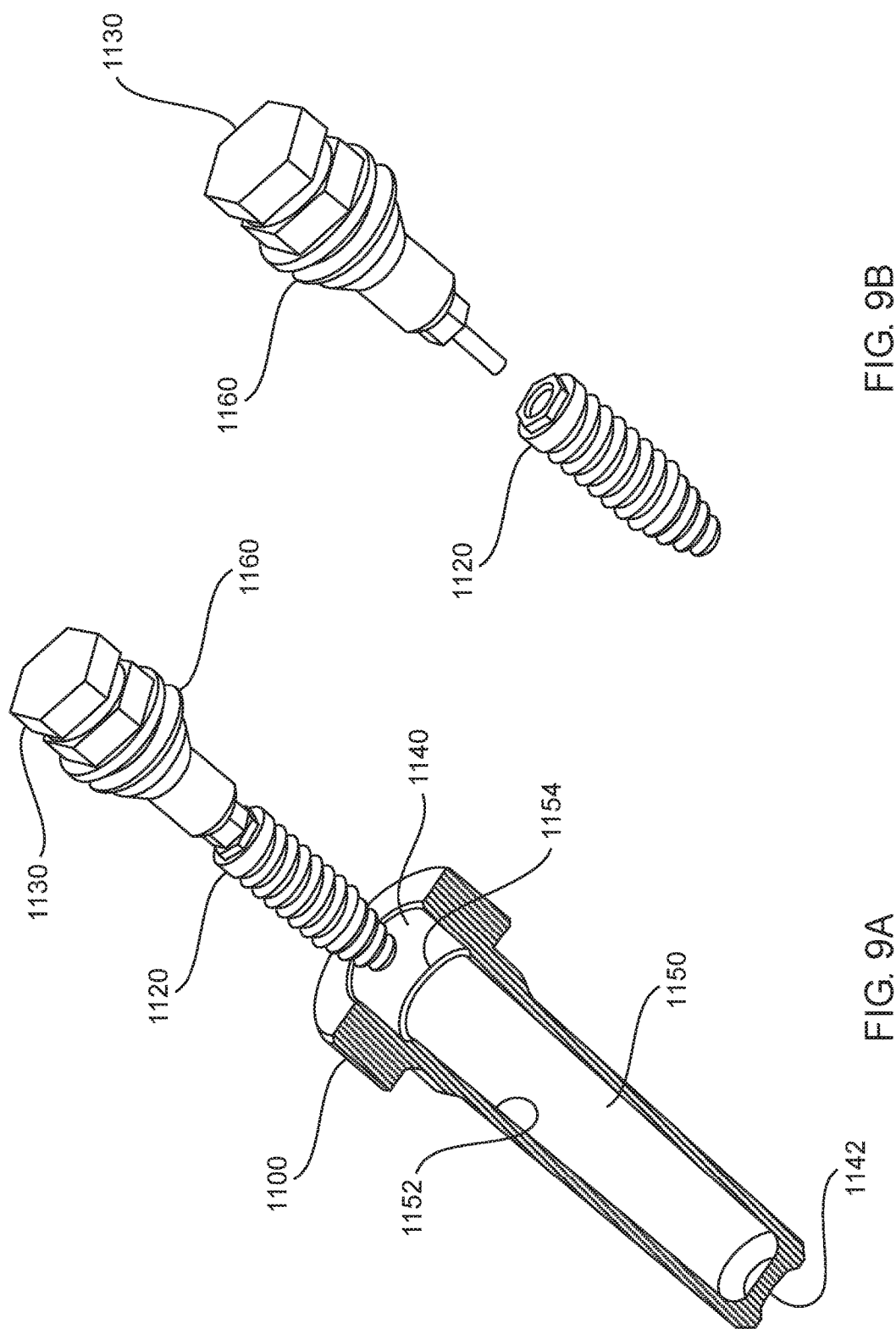

CONTAINER, APPARATUS AND METHOD FOR HANDLING AN IMPLANT

FIELD OF THE INVENTION

The invention, in some embodiments, relates to the field of handling an implant prior to using the implant in a body of a live subject and to related devices, apparatuses and methods.

BACKGROUND OF THE INVENTION

Plasma, and non-thermal plasma in particular, is known to affect surfaces of objects that are exposed to the plasma. Generally, plasma refers herein to ionized gas, including positively charged ions and negatively charged electrons, wherein the whole volume of the ionized gas is roughly neutral. Positively charged ions are generally referred to herein simply as "ions" whereas negatively charged electrons are referred to herein as "electrons". Neutral atoms and molecules are referred to as "neutrals".

Surfaces of objects exposed to plasma may often be affected so that some characteristics of the surface change following such exposure. It is believed that surface energy and chemistry may change due to the generation of reactive species in the plasma, and deposition of chemical substances on the surface. A featured result may be a modification of the surface properties. For example, plasma generated in a gaseous atmosphere comprising argon or helium with an admixture of oxygen, or even in air at low pressure, may render a surface of an object more hydrophilic.

SUMMARY OF THE INVENTION

When an object configured to be installed in a body of a live subject is exposed to plasma under certain conditions, biocompatibility of the object tends to improve. Such biocompatibility, associated with surface properties of the object, may include higher wettability, more suitable topography and improved drug delivery. For example, following suitable plasma treatment of an implant, hydrophilic properties of the surface of the implant tend to improve. Hydrophilic properties substantially enhance the wettability of the surface and improve the initial attachment of blood platelets to the treated implant. Consequently, better healing process may be achieved with substances that have been exposed to plasma prior to use.

The term "implant" is used herein for any object or substance which is to be installed in a body of a live subject in a medical procedure of implantation or installing or grafting, particularly such that is not autologous. Thus, "implant" may include an artificial implant such as an implant made of metal, e.g. a dental implant; or an implant made of polymer material such as silicone; or made of ceramic; or any combination thereof, for example an implant having metallic and ceramic parts "Implant" may also include biomaterial, where biomaterial is referred to herein as a substance which is configured to direct a diagnostic or therapeutic process in a body of a live subject, by controlling interactions with components of living system in the body. Examples of biomaterial may include bone graft used during a bone grafting procedure; polymers, and textile-based polymers in particular; hernia mesh, used in a hernia repair procedure; or collagen membrane used in dental surgery procedures.

Better healing process and faster and enriched osseointegration may be achieved with implants, bone graft or other biomaterial that have been exposed to plasma prior to installing ("osseointegration" herein means the direct structural and functional connection between a live bone and an artificial implant or bone graft or other biomaterial installed or used therewith). For example, Atmospheric plasma enhances wettability and cell spreading on dental implant metals (J Clin Periodontol 2012; 39: 400-407) by Duske et. al. describes significant reduction of contact angle of titanium discs (baseline values: 68°-117°) to close to 0°, irrespective of surface topography, after the application of argon plasma with 1.0% oxygen admixture for 60 s or 120 s. The cell size of osteoblastic cells grown on argon-oxygen-plasma-treated titanium discs was significantly larger than on non-treated surfaces irrespective of surface topography. As another example, D.-S. Lee et al. in Improvement of Hydrophilicity of Interconnected Porous Hydroxyapatite by Dielectric Barrier Discharge Plasma Treatment (IEEE Trans. Plasma Sci. 39 (11) 2166 (2011)) show that a dielectric barrier discharge (DBD) plasma treatment promotes hydrophilicity of interconnected porous calcium hydroxyapatite (IP-CHA) surfaces. Further, in Plasma Surface Modification of Artificial Bones for Bone Regeneration (published in ICPM 5, May 18-24, 2014, Nara, Japan), Moriguchil et. al. show that plasma-treatment can improve bone healing by IP-CHA, enhancing hydrophilicity of IP-CHA and its osteogenic potential in vitro. As yet another example, plasma surface treatment often improves biocompatibility of polystyrene cell culture surfaces, affecting adhesion and proliferation of cells cultures on such surfaces. For example, plasma surface modification of cell-culture materials may assist in establishing a stable culturing process for cells obtained from a patient's own body, for a later regeneration medicine process with the patient.

Augmentation mammoplasty involving the surgical implantation or emplacements of breast implants have a significant complication rate, involving for example a capsule contraction rate of up to 30%. Capsule contracture is believed to be promoted by infection at the implant site and around the implant. Plasma activation of the implant surface may reduce implant-induced contraction, for example by improving adhesion to the implant of antimicrobial liquids (such as antibiotics and antiseptic liquids) by employing submersion of the implant before implantation.

Notwithstanding the beneficial effects of plasma treatment discussed above, such beneficial effects of exposure to plasma on implant surfaces are often temporary, and demonstrated improved or enhanced healing decreases as the time interval between exposure of the implant to plasma and installing the implant in a body, increases. Such temporal deterioration often renders an activation of an implant by exposing the implant to plasma at the manufacturing site useless, because it may not be possible to ensure using the implant within a short period of time after the exposure to plasma, so as to maintain the benefits of such exposure.

There is thus provided according to an aspect of some embodiments a portable container for handling an implant, comprising a sealed compartment. The sealed compartment may be made in some embodiment of a dielectric material such as plastic or glass. According to some embodiments the sealed compartment may be made substantially of metal. The sealed compartment encloses an ionizable fluid of a pre-defined composition. An ionizable fluid stands for a fluid capable of being excited to plasma upon the application of a suitable electromagnetic field. According to some embodiments the fluid may be gas, comprising a predefined gaseous composition at a pre-defined pressure. According to some embodiments the fluid comprises a liquid having a predefined composition, such as a saline composition at a pre-defined concentration. The sealed compartment further contains therein at least one implant configured to be installed in a live subject. In some embodiments the implant may be metallic, typically being made from a hard alloy such as titanium or stainless steel. In some embodiments the implant may comprise metallic and non-metallic materials such as polymer materials or ceramics. In some embodiments the implant may be void of metal. In some embodiments the implant may comprise or consist of biomaterial intended to be used in a transplantation procedure, such as bone graft or other types of tissue or artificial substance used for grafting, or a combination thereof. The sealed compartment is configured to be opened by a user, thereby enabling removing the implant from the portable container.

The portable container further comprises at least one electrode made of an electrical conductive material, electrically associated with an electric conductor outside the sealed compartment and configured for applying a plasma generating electric field inside the sealed compartment.

The portable container is configured to enable storing the implant inside the sealed compartment, shipping the portable container with the implant being stored therein, and, without breaking the seal of the sealed compartment nor interfering with the pre-defined composition of the fluid, generating plasma in the fluid using an electric field, thereby surface-treating the implant. According to an aspect of some embodiments, the portable container may be used to seal the implant in an ionizable medium consisting substantially of the pre-defined fluid inside the sealed compartment of the portable container. Such sealing of the implant may be carried out after the manufacturing process of the implant, optionally at the implant manufacturing site. According to some embodiments such sealing may be carried out prior to storing the implant or prior to shipping the implant or prior to distributing the implant to users.

The implant may also be sterilized at the implant manufacturing site before disposing into the sealed compartment or after disposing into the sealed compartment (e.g. using gamma radiation). Alternatively or additionally, the implant may be sterilized by the plasma treatment inside the sealed compartment according to the teachings herein, prior to use. The implant inside the portable container may then be stored for a few days or a few weeks or for a few months or even for years—and then may be taken for use, e.g. in a medical treatment site.

By being portable it is meant that the portable container is configured and capable of being shipped or transported easily, without damaging the implant nor the composition of the fluid inside the sealed compartment. For economic reasons, the portable container is configured to be light-weighted and small in size whereas the portable container dimensions generally correspond to the dimensions of the implant intended to be stored therewith. For example, a portable container for a single dental implant may have a generally elongated cylindrical shape of less than 3 cm in diameter and less than 15 cm in length and even less than 2 cm in diameter and less than 10 cm in length. As another example, a portable container for a breast implant may have the largest dimension as small as 30 cm and even as small as 20 cm.

Prior to use, e.g. when in a medical treatment site, the portable container may be activated for generating plasma within the sealed compartment and in the vicinity of the implant. For example, the portable container may be electrically associated with a an activation device, the activation device being configured and operable for generating an electromagnetic (EM) field suitable for exciting plasma in the sealed compartment. The activation device may include for example an RF generator and an amplifier configured for generating high voltage—e.g. above 100V or even above 1 KV. The generated RF high voltage may be supplied to electrodes that generate the plasma activating field in the sealed compartment.

Plasma may be generated by turning on the electric circuit, resulting in plasma-treating the implant inside the sealed compartment, thereby preparing the implant for installment. Then the plasma generation may be stopped. If for any reason the sealed compartment is not opened after the plasma generation and maintained sealed, plasma generation can be repeated, e.g. by turning on the electric circuit again, as described above. After plasma treating the implant is concluded, the sealed compartment may be opened and the implant may be taken to be installed.

The sealed compartment may include a sealable opening for implant insertion and extraction which can be sealed after closing. The sealed compartment may include therein a holder which is configured to hold an implant such as a dental implant or any other type of implant. The holder may include an electrical conductor electrically connected to the implant thereby allowing electrical connectivity to the implant. The sealed compartment may further include a tap so that after an implant is inserted to the sealed compartment, the tap may be used to fill the compartment with a desired composition of fluid or to evacuate the compartment, and may afterwards be closed and sealed. In some embodiments, the tap may be a part of the sealable opening.

According to some embodiments, the portable container may further be used for generating plasma inside the sealed compartment, by applying a plasma-generating electromagnetic (EM) field inside the sealed compartment. Such generation of plasma may be assisted by the electrode of the portable container which is configured for applying a plasma generating electric field inside the sealed compartment. Such generation of plasma may further be adapted for treating surfaces of the implant inside the sealed compartment so as to obtain desired effects on the surface or to obtain desired surface characteristics or qualities such as improved wettability, or to improve acceptance of the implant in the body of the living subject and improve healing according to specified criteria.

Following the plasma generation step, the sealed compartment may be opened and the implant may be removed and taken for use. Opening the sealed compartment may be carried out by any of various techniques. For example opening a cover which is configured to be closed (during sealing the sealed compartment) and opened, or by controllably braking a portion of the sealed compartment, for example in case the sealed compartment is formed as a sealed glass tube. According to some embodiments opening the sealed compartment may be carried out substantially immediately following the plasma generation step. According to some embodiments opening the sealed compartment may be carried out substantially immediately prior to installing the implant in the body of a living subject. According to some embodiments generating the plasma and opening the sealed compartment may be done at the medical treatment site, where installing the implant is to be performed.

To conform to sterility standards related to handling an implant prior to installment in a live subject, plasma activation is performed in a non-sterile environment (e.g. a non-sterile room and using hands and tools that have not necessarily been sterilized). Then the portable container is carried, e.g. using unsterilized tools or hands, into sterile surroundings. The sterile implant may then be removed from the sealed compartment and disposed onto a sterile tray for the use of a surgeon, or directly to the sterile hands of a surgeon or the like. According to some embodiments the portable container may comprise an external capsule and an internal capsule contained in the external capsule and containing the implant therein. At least one of the external capsule and the internal capsule may function as the sealed compartment according the teachings herein. Following plasma treatment, the external capsule may be opened for removing the internal capsule with the implant therefrom. Then, in the sterile environment and using sterile tools and hands, the internal capsule may be opened and the sterile implant may be extracted therefrom to be installed in the patient.

The sealed compartment may be sealed, for maintaining the pressure and composition of the fluid there inside. Various levels of sealing are contemplated. In some embodiments the fluid inside the sealed compartment may be liquid, e.g. a saline at a pre-defined concentration, and the sealing of the sealed compartment is configured to prevent escape of the liquid out from the sealed compartment. In some embodiments the fluid inside the sealed compartment is a gas at a pre-defined composition and a pre-defined pressure. For example, the sealed compartment may contain Argon or air at a low pressure, e.g. less than 0.02 At or even less than 0.01 At. In some embodiments, retaining the pressure and composition of the atmosphere inside the sealed compartment means allowing a variation of no more than 20% or no more than 10% or no more than 2% or even no more than 1% of the initial pressure inside the sealed compartment. In some embodiments the sealed compartment may be configured to retain a low pressure at a pre-defined composition for a period of more than 5 years.

In some embodiments the sealed compartment may be configured to retain the atmosphere there inside for a much shorter period than several years, e.g. for a period of several days, for example two days. In some such embodiments the portable container may be kept inside a sealed package during storing, thereby not being directly exposed to room atmosphere. In some embodiments the portable container may be sealed, e.g. vacuum-sealed, inside a lamination bag, e.g. an aluminum-coated lamination bag, for storing. The sealed compartment may then be maintained unexposed to room atmosphere for a possibly long period of storing, being exposed to room atmosphere only after tearing the vacuum-sealed bag, prior to use. Following tearing the vacuum-sealed bag the portable container is taken for plasma treatment of the implant as described above, typically within minutes after opening the sealed package (the vacuum-sealed bag), thus the atmosphere inside the sealed compartment is not impaired.

According to some embodiments the devices, apparatuses and methods disclosed herein are suitable for implants intended to be installed in humans. According to some embodiments the implant may be metallic. According to some embodiments the implant may be substantially made of one of the following metals, or from alloys comprising one or more of the following metals: titanium, stainless still, gold and platinum. According to some embodiments the implant may be a dental implant.

According to some embodiments the portable container further comprises an electrical circuit electrically associated with the electrode or electrodes of the portable container. The electrical circuit is configured to provide to the electrode electric power suitable for applying a plasma generating electric field in the sealed compartment. According to some embodiments the electric circuit is configured to consume energy from a portable electric DC source such as a battery or a pack of batteries, thereby being operable as a stand-alone plasma generator.

According to some embodiments the portable container may be disposed in a slot of an activation device which is configured to receive the portable container. The activation device may comprise an electrical circuit which associates electrically with the electrode of the portable container when the portable container is received in the slot. The electrical circuit is configured to provide to the electrode or electrodes of the portable container electric power suitable for applying a plasma generating electric field in the sealed compartment, when the portable container is disposed in the slot.

Thus, according to some embodiments, the sealed compartment may be sealed, with an implant there inside, in a manufacturing site, may be then stored for a few days or weeks or for months or even for years—and then may be taken for use. The portable container may be placed in the slot of the activation device, the activation device being operated in a medical treatment site. Plasma may be generated by turning on the electric circuit, resulting in treating the surface of the implant inside the sealed compartment, thereby preparing the implant for installing. Then the portable container may be removed from the activation device, the sealed compartment may be opened and the implant may be taken to be installed.

According to a further aspect of some embodiments there is provided an apparatus for plasma treatment of an implant prior to installing the implant in a living subject. The apparatus comprises an activation device, which comprises a slot configured to receive a portable container. The portable container may comprise a sealed compartment enclosing a fluid, and may further contain therein at least one implant configured to be installed in a live subject. The sealed compartment is also configured to be opened, thereby enabling removing the implant from the portable container. The activation device further comprises an electrical circuit configured to be electrically associated with at least one electrode and configured to provide to the at least one electrode electric power suitable for applying a plasma generating electric field in the sealed compartment, when the portable container is disposed in the slot.

Gaseous composition inside the container may be at atmospheric pressure (about 100 KPa), at a pressure lower than atmosphere or a pressure higher than atmosphere. For example, the gas can be at a pressure of 0.8 KPa for facilitation of plasma ignition. Helium gas will ignite in a distance of 1 cm between electrodes at an RF field (between 1 MHz and 15 MHz) of about 7 KV in atmospheric pressure and at a voltage of about 200V in 0.8 KPa.

According to some embodiments a dielectric breakdown discharge (DBD) mode of operation may be used to excite the plasma. According to some embodiments plasma may be excited by an electromagnetic (EM) field generated between at least two electrodes. According to some embodiments the EM field may be generated at a frequency above 10 KHz. According to some embodiments the field may have a radio frequency (RF) in the range between 0.1 MHz and 20 MHz, for example at 500 KHz. According to some embodiments the field may be in the VHF range, e.g. between 20 MHz and 300 MHz. According to some embodiments the field may be in the UHF range, e.g. between 300 MHz and 3 GHz. According to some embodiments the field may be in the microwave SHF range, e.g. between 3 GHz and 30 GHz. According to some embodiments the field may be in the microwave EHF range, e.g. between 30 GHz and 300 GHz.

According to some embodiments the portable container is configured to allow plasma excitation at voltages lower than 10 KV.

The terms plasma generation, plasma activation, plasma maintaining and plasma inducing may be used herein interchangeably, refereeing generally to the process of sufficiently ionizing the fluid inside the sealed compartment using a suitable EM Field to establish a plasma state (e.g such as a glow discharge) of the fluid. The term plasma ignition refers more specifically to the first instant of plasma generation.

Two conductors are said herein to be electrically isolated or electrically disconnected if there is no Ohmic (DC) electrical conductance between the conductors.

This invention provides a portable container having an artificial implant or biomaterial such as bone graft sealed in a sealed compartment therein, being immersed in an ionizable fluid having a pre-defined composition configured for plasma activation by an EM field.

This invention provides a portable container containing the implant as described above, the portable container being configured for transportation, shipping and storing without breaking the seal of the sealed compartment and without interfering with the composition of the fluid therein.

This invention provides a portable container containing the implant as described above, the portable container being further configured for plasma activation of the fluid in the sealed compartment after such transportation or shipping or storing, without breaking the seal of the sealed compartment and without interfering with the composition of the fluid therein.

This invention provides a portable container configured as a "plug and play" article, enabling plasma-treating the implant stored there inside at a medical treatment site just prior to using the implant, by disposing the portable container in a slot of a plasma activation device and turning on the plasma activation device.

This invention provides a portable container which can be used for storing an implant after manufacturing, possibly for a period of several months or several years, transporting the implant to a medical treatment site, plasma-treating the implant inside the sealed compartment of the portable container at the medical treatment site for a duration of several seconds or several minutes, and taking the implant for use substantially immediately after the plasma treatment.

This invention provides a portable container which can be used for enabling and supporting a significant increase of quality and success rates of medical procedures involving installment, implantation, emplacement and grafting of artificial implants and biomaterial such as bone graft. This invention separately provides an apparatus including a portable container such as described above and an activation device suitable for activating plasma in the sealed compartment of the portable container.

This invention separately provides a method of handling an implant, the method enables for plasma-treating an implant just prior to a medical procedure, e.g. in a medical treatment site, using a simple plasma activation device that has no pumping or other fluid transportation capabilities, thereby enabling and supporting a significant increase of quality and success rates of medical procedures involving installment, implantation, emplacement and grafting of artificial implants and biomaterial such as bone graft.

Certain embodiments of the present invention may include some, all, or none of the above advantages. Further advantages may be readily apparent to those skilled in the art from the figures, descriptions, and claims included herein.

Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 6A schematically depicts an electrical configuration suitable for plasma generation in a sealed compartment of a portable container, containing an implant;

FIG. 6B schematically depicts another electrical configuration suitable for plasma generation in a sealed compartment of a portable container, containing an implant;

FIG. 6C schematically depicts yet another electrical configuration suitable for plasma generation in a sealed compartment of a portable container, containing an implant;

FIG. 9A schematically depicts a cross-section of the internal capsule of the portable container of FIG. 8A in a semi exploded view, with the dental implant attached to the insertion driver;

FIG. 9B schematically depicts the dental implant and the insertion driver of FIG. 9A in an exploded view;

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation.

Figure 1:
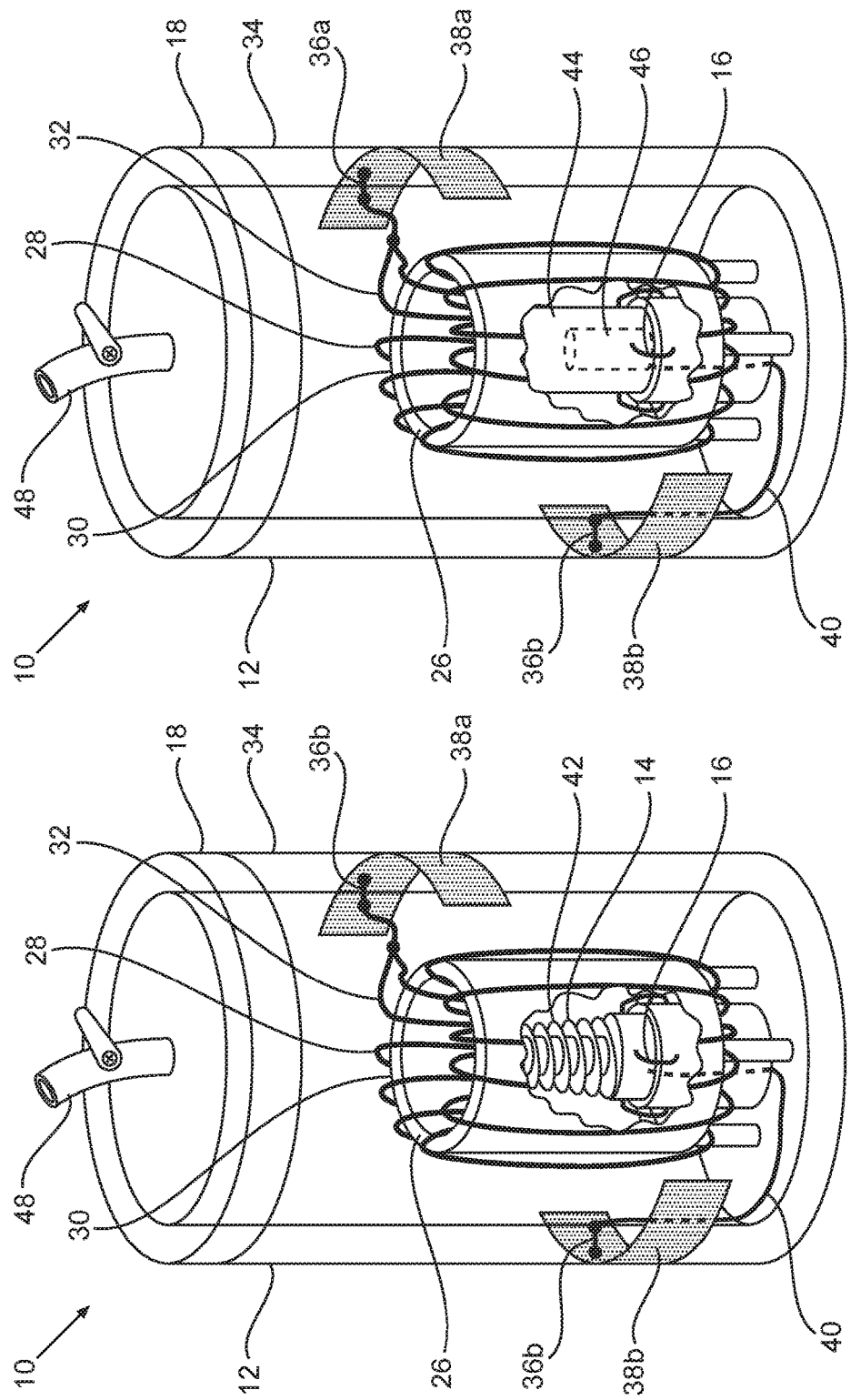
FIG. 1A schematically depicts an embodiment of a portable container for handling an artificial implant, according to the teachings herein.
FIG. 1B schematically depicts an embodiment of the portable container of FIG. 1A, used for handling biomaterial, according to the teachings herein.

FIG. 1A schematically depicts an embodiment of portable container 10 for handling an artificial implant. Portable container 10 comprises a sealed compartment 12. According to some embodiments sealed compartment 12 is made of a dielectric material such as a polymer material or glass. According to some embodiments sealed compartment 12 is made of a transparent material e.g. from Perspex, so as to allow a user to see the plasma glow when plasma is generated therein. According to some embodiments sealed compartment 12 is made of metal. The sealed compartment encloses a fluid. The fluid composition is configured to allow plasma ignition and plasma maintaining by an electromagnetic field as is further explained and described below.

In some embodiments the fluid is a gaseous atmosphere of a pre-defined composition of gases at a pre-defined pressure. In embodiments including gaseous atmosphere inside the sealed compartment the gas composition may include helium, or argon or oxygen or nitrogen or air or combination thereof. The pressure inside the sealed compartment may be lower than one atmosphere, e.g. in the range of 0.1-1 Torr, or in the range of 1-10 Torr or in the range of 10-100 Torr. In some embodiments the pressure in the sealed compartment may be about one atmosphere. In some embodiments the pressure in the sealed compartment may be higher than one atmosphere. Typically, the gas composition, the gas pressure and the EM field employed to generate plasma inside the sealed compartment are interdependent factors selected so as to enable plasma generation in a desired mode of operation.

In some embodiment the fluid consists substantially of liquid. In embodiments including liquid inside the sealed compartment the liquid composition may include water or saline or other liquid and may include surface treatment additives or wound healing or bone growth factors such as factor-beta, acidic and basic fibroblast growth factor, platelet-derived growth factor, and bone morphogenetic protein substances to be deposited on the implant.

Sealed compartment 12 further contains an implant 14 configured to be installed in a live subject. The implant is held fixedly inside the sealed compartment by holders 16, configured to hold the implant steadily while covering only a small surface area of the implant, thereby enabling exposure to plasma to a relatively large portion of the implant surface. In some embodiments the implant inside the sealed compartment may be attached to a part which is not intended to be installed together with the implant, such as an insertion driver in a dental implant. In some embodiments, the implant is held in the sealed compartment by the insertion driver or by any other such part attached thereto. According to some embodiments implant 14 may include metallic parts or metallic surfaces or may otherwise have electrically conductive parts, thereby being suitable to be used as one of the plasma generating electrodes inside sealed compartment 12.

Sealed compartment 12 comprises a cover 18 which is sealingly closed when the sealed compartment is sealed, and is configured to be opened by a user, thereby enabling removing the implant from the portable container.

The portable container further comprises a first electrode 26. First electrode 26 comprises an electrode conductor 28 wound around a cylindrical core 30 made of a dielectric, non-magnetic material, electrode conductor 28 having both ends electrically interconnected. First electrode 26 is disposed inside the sealed compartment, substantially surrounding the implant. Electrode conductor 28 is electrically connected to an electric conductor 32 such as an electric wire which extends through a wall 34 of the sealed compartment e.g. via a sealed feed-though 36a, and is electrically connected to a first contact 38a. First contact 38a is located outside sealed compartment 12, on an external surface of the sealed compartment, being thereby accessible for electrical connection from outside the sealed compartment.

The portable container optionally comprises a second contact 38b on the external surface of the sealed compartment, being electrically connected to a second electric conductor 40 extending through wall 34 of the sealed compartment, e.g. via a sealed feed through 36b. Second electric conductor 40 may in some embodiments be electrically contacted to implant 14, the implant may thereby be employed as a second electrode 42. According to some embodiments, second electric conductor comprises a contacting surface (not shown in this Figure) configured to contact implant 14 when implant 14 is suitably positioned inside sealed compartment 12. By applying a suitable electric filed between first electrode 26 and second electrode 42, plasma may be generated within sealed compartment 12, in surroundings adjoining implant 14.

According to some embodiments portable container 10 does not include a second electrode, being void of, e.g. second contact 38b and second conductor 40. According to some embodiments implant 14 is electrically disconnected from a power source. According to some embodiments plasma is generated in sealed compartment 12 using only a single electrode, that is to say first electrode 26, in an Inductive Coupled Plasma (ICP) mode of operation.

In some embodiments the electric conductors 32 and 40 between first electric contact 38a and first electrode 26, and between second electric contact 42b and the implant, respectively, are insulated to avoid arcing. According to some embodiments electrode conductor 28 is insulated to avoid arcing. According to some embodiments electrode conductor 28 is insulated to generate plasma in a dielectric breakdown discharge (DBD) mode of operation. According to some embodiments electrode conductor 28 is not insulated, at least along a portion thereof, thereby being configured for generating plasma substantially in an arcing or corona discharge or in a Capacitance Coupled Plasma (CPS) mode of operation.

Plasma may be generated inside sealed compartment 12 by applying a radio-frequency (RF) electromagnetic (EM) field at a suitable magnitude between the first electrode 26 and the second electrode 42, namely the implant 14, for example by supplying an RF voltage substantially between electric contact 38a and electric contact 38b as is known in the art and is further described and detailed herein below.

According to some embodiments implant 14 may be electrically non-conductive, namely made of a dielectric material such as non-conductive polymer or ceramic According to some such embodiments second conductor 40 may function as an electrode or may be connected or otherwise be electrically associated with an electrode. For example second electric conductor 40 may be connected to a small metal segment such as a metal plate (not shown in this Figure) positioned underneath the implant. According to some such embodiments, plasma may be generated upon the application of a plasma-generating EM field, in the region substantially between the electrodes and around the implant.

FIG. 1B schematically depicts an embodiment of portable container 10 used for handling, storing, shipping and plasma treating biomaterial. Sealed compartment 12 in FIG. 1B contains a canister 44 comprising biomaterial therein. The canister is held fixedly inside the sealed compartment by holders 16, configured to hold the canister steadily. Canister 44 may be made of a dielectric material. According to some embodiments a contacting surface of second electric conductor 40 (such as an electrically exposed end of the conductor) is employed as second electrode 42, so that plasma may be generated in a space between the first electrode 26 and the second electrode 42, including in a space inside canister 44. According to some embodiments, canister 44 may further comprise a metal segment 46, being in electrical contact with second electric conductor 40 when canister 44 is suitably positioned inside sealed compartment 12. According to some embodiments, the metal segment 46 may extend between the outside of canister 44 to the inside thereof. According to some embodiments, metal segment 46 may have a shape of an elongated rod extending inside canister 44 and through the bottom thereof, being thereby configured to be employed as second electrode 42 inside canister 44. According to some embodiments the elongated rod inside canister 44 is electrically isolated in the portion thereof inside the canister, thereby being electrically isolated from the biomaterial therein. According to some embodiments the elongated rod is not insulated inside the canister.

Figure 2:
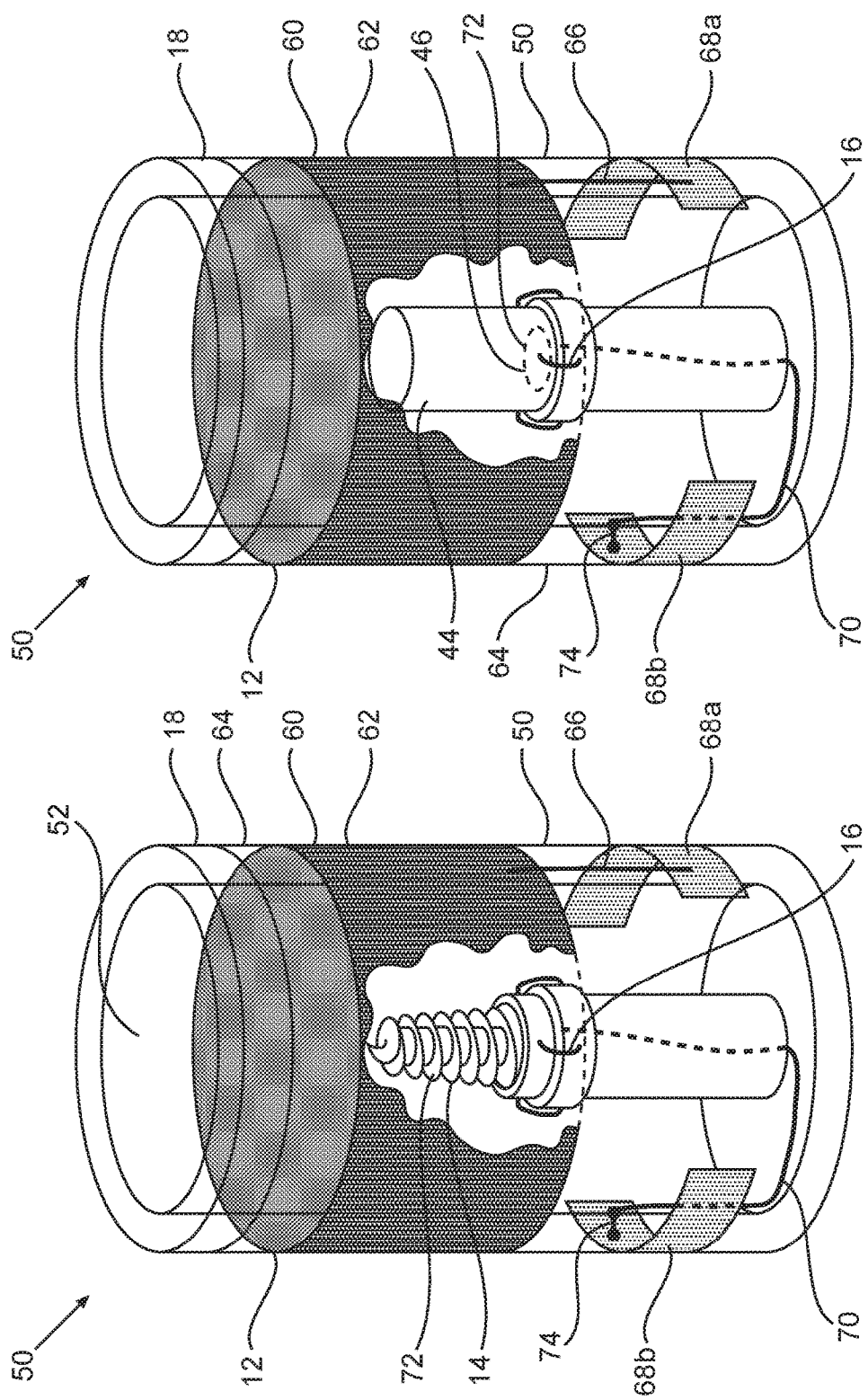
FIG. 2A schematically depicts an embodiment of another portable container for handling an artificial implant, according to the teachings herein.
FIG. 2B schematically depicts an embodiment of the portable container of FIG. 2A, used for handling biomaterial, according to the teachings herein.

FIG. 2A schematically depicts an embodiment of a portable container 50 for handling an implant. Portable container 50 comprises a sealed compartment 52. Portable container 50 is different from portable container 10 in that plasma is generated in sealed compartment 52 between two electrodes wherein one of the electrodes is inside the sealed compartment and one electrode is outside the sealed compartment. Similarly to sealed compartment 12, sealed compartment 52 may be made of a dielectric material such as a polymer material or glass and/or of a transparent material such as Perspex. The sealed compartment encloses a fluid, the composition of which is configured to allow plasma ignition and plasma maintaining by an electromagnetic field as is further explained and described below. The fluid in sealed compartment 52 may be gaseous or liquid, substantially similarly to the fluid in sealed compartment 12.

Sealed compartment 52 contains an implant 14 configured to be installed in a live subject. The implant may be held fixedly inside the sealed compartment so that only surface area of the implant which is not intended to be subject to plasma treatment is concealed. For example, the implant inside the sealed compartment may be attached to a part which is not intended to be installed together with the implant, such as an insertion driver in a dental implant, whereas the area of the dental implant contacting the insertion driver is not intended to integrate with the live body the implant is installed in. In some embodiments, the implant is held in the sealed compartment by the insertion driver or by any other such part attached thereto. According to some embodiments implant 14 may include metallic parts or metallic surfaces or may otherwise have electrically conductive parts, thereby being suitable to be used as the plasma generating electrode inside sealed compartment 52.

Portable container 50 further comprises a first electrode 60. First electrode 60 comprises a cylindrical ring 62 enveloping sealed compartment 52 and facing implant 14. Cylindrical ring 62 is positioned on an external surface of the sealed compartment, being thereby electrically insulated by a sealed compartment wall 64 from the fluid inside the sealed compartment. First electrode 60 is electrically connected via an electric conductor 66 such as an electric wire, to a first contact 68a on the external surface of the sealed compartment.

Portable container 50 further comprises a second contact 68b on the external surface of the sealed compartment, electrically connected to a second electric conductor 70 extending through wall 64 of the sealed compartment, e.g. via a sealed feed through 74. Second electric conductor 70 is electrically connected to implant 14, the implant being thereby adapted to be employed as a second electrode 72. According to some embodiments, second electric conductor 70 comprises a contacting surface (not shown in this Figure) configured to contact implant 14 when implant 14 is suitably positioned inside sealed compartment 52. By applying a suitable electric filed between first electrode 60 and second electrode 72, plasma may be generated within sealed compartment 12, in an immediate surroundings of implant 14.

By applying a suitable electric filed between first electrode 60 and second electrode 72, plasma may be generated within sealed compartment 52. According to some embodiments plasma may be generated inside sealed compartment 52 by applying a DC field at a suitable magnitude between the first electrode 60 and the second electrode 72, namely the implant 14, for example by supplying a DC voltage substantially between electric contact 68a and electric contact

68b. According to some embodiments plasma may be generated inside sealed compartment 52 by applying an AC field such as a radio-frequency (RF) electromagnetic (EM) field at a suitable magnitude between the first electrode 60 and the second electrode 72, namely the implant 14, for example by supplying an RF voltage substantially between electric contact 68a and electric contact 68b as is known in the art and is further described and detailed herein below.

In some embodiments the electric conductors 66 and 70 between first electric contact 68a and first electrode 60, and between second electric contact 68b and the implant, respectively, are insulated. According to some embodiments the first electrode 60 is separated and electrically insulated from the plasma generation region inside sealed compartment 52 by wall 64 of sealed compartment 52, thereby allowing plasma generation in a DBD mode of operation. According to some embodiments first electrode 60 is disposed inside the sealed compartment, at least along a portion thereof, thereby having electric contact with the fluid inside sealed compartment 52 and being thereby configured for generating plasma substantially in an arcing or corona discharge or in a Capacitance Coupled Plasma (CPS) mode of operation.

Portable container 50 may be used for handing, shipping, storing and plasma-treating biomaterial such as bone graft, rather than an implant, as discussed above. Examples of biomaterial may include bone graft used during a bone grafting procedure, polymers and textile-based polymers in particular, hernia mesh, used in a hernia repair procedure, or collagen membrane used in dental surgery procedures. Such biomaterial may be provided in various forms and appearances such as powder, crushed granules, putty, chips, gel and paste. When provided as a dry powder, granulates or chips, gaseous atmosphere may be preferred as an ionizable medium surrounding the biomaterial, to enhance the effect of surface treatment to each individual particulate. According to some embodiments bone graft powder, granulates or chips may be immersed in ionizable liquid and plasma-treated therein, optionally followed with a drying step carried out after the plasma treatment. Dry biomaterial, liquid, gel or paste may be disposed directly in sealed compartment 52, whereas implant 14 is replaced by second electrode 72 made of an electrically conducting material, having a shape of e.g. a cylinder positioned along the central axis of sealed compartment 52 and electrically connected to second conductor 70. Biomaterial inside sealed compartment 52 may thus be subject to plasma treatment as plasma is generated inside sealed compartment 52 substantially between first electrode 60 and second electrode 72.

FIG. 2B schematically depicts an embodiment of portable container 50 used for handling, storing, shipping and plasma treating biomaterial. Sealed compartment 52 in FIG. 2B contains canister 44 comprising biomaterial therein. According to some embodiments a contacting surface of second electric conductor 70 (such as an electrically exposed end of electric conductor 70) is employed as second electrode 72, so that plasma may be generated in a space between the first electrode 60 and the second electrode 72, including in a space inside canister 44. According to some embodiments, canister 44 may further comprise a metal segment 46, being in electrical contact with second electric conductor 70 when canister 44 is suitably positioned inside sealed compartment 52. According to some embodiments, the metal segment 46 may extend between the outside of canister 44 to the inside thereof. According to some embodiments, metal segment 46 may have a shape of an elongated rod extending inside canister 44 and through the bottom thereof, being thereby configured to be employed as second electrode 42 inside canister 44. According to some embodiments plasma may be generated between first electrode 60 and elongated rod 46 of canister 44, e.g. inside canister 44 and in a surroundings adjoining the biomaterial therein.

Figure 3:
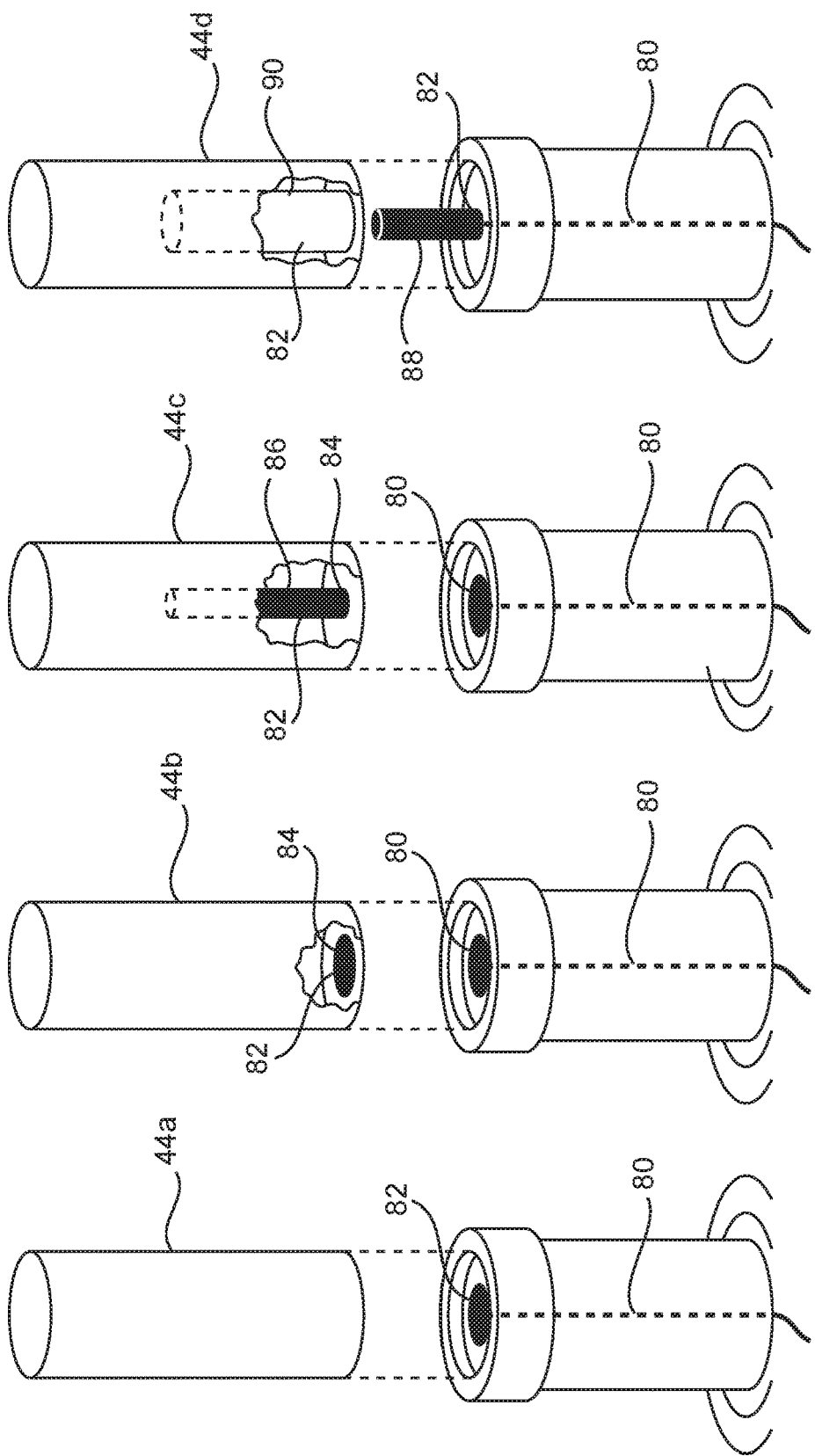
FIG. 3A schematically depicts an embodiment of a canister, made of a dielectric material, for storing and plasma treating biomaterial inside a portable container of the invention.
FIG. 3B schematically depicts an embodiment of a canister, made of a dielectric material and having a metal segment, for storing and plasma treating biomaterial inside a portable container of the invention.
FIG. 3C schematically depicts an embodiment of a canister, made of a dielectric material and having a metallic cylindrical electrode inside, for storing and plasma treating biomaterial inside a portable container of the invention.
FIG. 3D schematically depicts an embodiment of a canister, made of a dielectric material and having cylindrical shroud, for storing and plasma treating biomaterial inside a portable container of the invention.

FIGS. 3A-3D depict schematically four different embodiments of a canister for storing and plasma treating biomaterial inside a portable container of the invention, e.g. the portable container of FIG. 1B or the portable container of FIG. 2B. FIG. 3A depicts an exploded view of a canister 44a, and a portion of a sealed compartment of the invention according to the teachings herein. Canister 44a is made substantially of a dielectric material and is configured to be supported inside a sealed compartment, e.g. sealed compartment 12 or sealed compartment 52, substantially similarly to canister 44. The portable container comprises a second electric conductor 80, electrically coupled to a second electrode 82, whereas canister 44a is configured to be supported inside the sealed compartment adjacent to the second electrode 82. Upon employing a plasma-generating EM field plasma may be generated in a space between a first electrode (not shown in this Figure) and the second electrode 82, including in a space within canister 44a.

FIG. 3B depicts an exploded view of a canister 44b, according to the teachings herein. Canister 44b is made substantially of a dielectric material and further comprises a metal segment 84, having a shape of a disk, extending between the outside and the inside of the canister in a bottom side thereof. When canister 44b is supported inside a portable container of the invention metal segment 84 is electrically coupled to a second electric conductor 80, thereby being configured to be employed as a second electrode 82. Accordingly, plasma may be generated upon employing a plasma-generating EM filed between a first electrode (not shown in this Figure) and the second electrode 82, including within canister 44b. Metal segment 84 may in some embodiments be insulated by a dielectric layer on a portion thereof inside canister 44b, thereby being insulated from the biomaterial stored in the canister.

FIG. 3C depicts an exploded view of a canister 44c, according to the teachings herein. Canister 44c is made substantially of a dielectric material and further comprises a metal segment 84, having a shape of a rod 86, extending from the outside of the bottom of the canister to the inside and along the canister. When canister 44c is supported inside a portable container of the invention, rod 86 is electrically coupled to the second electric conductor 80, thereby being configured to be employed as a second electrode 82. Accordingly, plasma may be generated upon employing a plasma-generating EM field between a first electrode (not shown in this Figure) and the rod 86, including within the canister. Rod 86 may in some embodiments be insulated by a dielectric layer on a portion thereof inside canister 44c, thereby being insulated from the biomaterial stored therein.

FIG. 3D depicts an exploded view of a canister 44d, and a portion of a portable container of the invention according to the teachings herein. Canister 44d is made substantially of a dielectric material and is configured to be supported inside a portable container, e.g. portable container 10 or portable container 50, substantially similarly to canister 44. The portable container comprises a second electric conductor 80, extending into a second electrode 82 having a shape of an elongated rod 88. Canister 44d comprises a shroud 90 positioned and dimensioned to house rod 88 when canister 44d is suitably supported inside the portable container. Upon employing a plasma-generating EM field plasma may be generated in a space between a first electrode (not shown in this Figure) and the second electrode 82, including in a space within canister 44*d*.

According to some embodiments, canisters of the invention (such as canisters 44, 44*a*, 44*b*, 44*c* and 44*d*) may be sealed. According to some embodiments, sealed canisters may contain biomaterial immersed in a fluid adapted to be ionized and excited to plasma when subject to a suitable electromagnetic field, substantially as described above. The fluid in the sealed canister may be a liquid at a pre-defined composition or a gas at a pre-defined composition and a pre-defined pressure, as described above for the fluid inside the sealed compartments of the invention. According to some embodiments a sealed canister contained in a sealed compartment may contain an ionizable fluid such as a low pressure gaseous composition, whereas the space outside the sealed canister may not be suitable for plasma generation. In other words, in some embodiments the sealed compartment contains only in a portion thereof, i.e., inside the sealed canister, fluid configured to be excited to plasma when subject to a plasma-generating EM field, whereas plasma may be generated in other portions of the sealed compartment.

Figure 4:
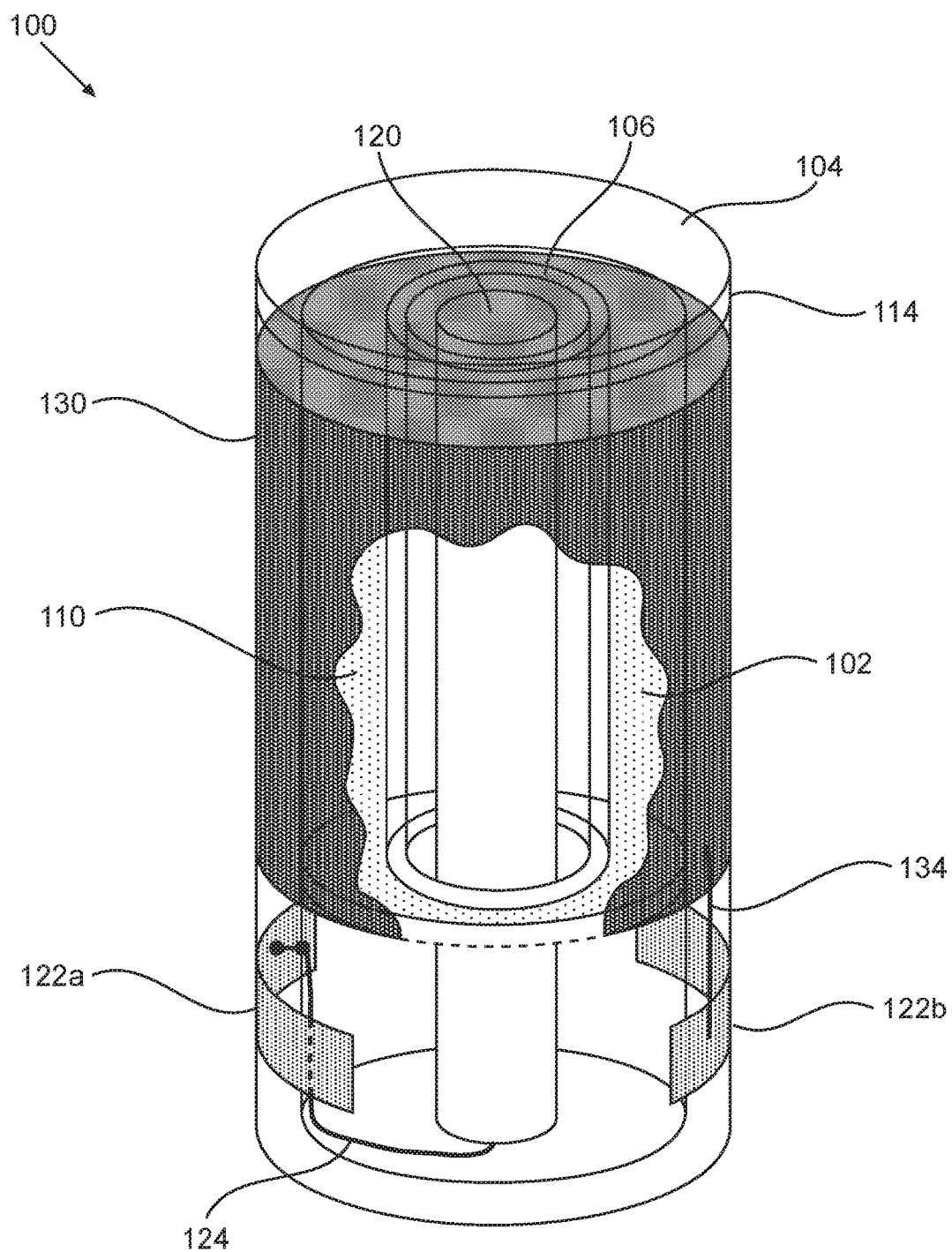
FIG. 4 schematically depicts an embodiment of a portable container for handling biomaterial such as bone graft.

FIG. 4 schematically depicts an embodiment of portable container 100 for handling biomaterial such as bone graft. Portable container 100 comprises a sealed compartment 102. Sealed compartment 102 is shaped as a cylindrical ring, being confined by an external cylinder 104 and an internal cylinder 106. According to some embodiments sealed compartment 102 is made of a dielectric material such as a polymer material, plastic or glass. According to some embodiments sealed compartment 102 may comprise metallic parts. According to some embodiments sealed compartment 102 may be transparent, e.g. from Perspex, at least in parts thereof, so as to allow a user see the plasma glow when plasma is generated therein.

The sealed compartment encloses a fluid. The fluid composition is configured to allow plasma ignition and plasma maintaining by an electromagnetic field as is further explained and described below. The fluid inside sealed compartment 102 may be gaseous or liquid, substantially as described above concerning the fluid inside sealed compartment 12 and sealed compartment 52. In embodiments including liquid inside the sealed compartment the liquid composition may include water or saline or other liquid and may include surface treatment additives or wound healing or bone growth factors such as factor-beta, acidic and basic fibroblast growth factor, platelet-derived growth factor, and bone morphogenetic protein substances.

The sealed compartment further contains biomaterial 110 such as bone graft, disposed between the external cylinder and the internal cylinder. Biomaterial 110 may be in a form of powder, crushed granules, putty, chips, gel and paste.

Sealed compartment 102 comprises a cover 114 which is sealingly closed when the sealed compartment is sealed, and is configured to be opened by a user, thereby enabling removing the biomaterial from the portable container.

Portable container 100 further comprises a first electrode 120. First electrode 120 comprises an elongated rod extending concentrically along the axis of internal cylinder 106. First electrode 120 is electrically connected to a first electric contact 122*a* via an electric conductor 124. Portable container 100 further comprises a second electrode 130, electrically connected to a second electric contact 122*b* via an electric conductor 134. First electric contact 122*a* and second electric contact 122*b* are located on an external surface of the sealed compartment, i.e. on the external surface of external cylinder 104, thereby being accessible for contact from the outside of sealed compartment 102.

Plasma may be generated inside sealed compartment 102 by applying a radio-frequency (RF) electromagnetic (EM) field at a suitable magnitude between first electrode 120 and second electrodes 130, for example by supplying an RF voltage substantially between electric contact 122*a* and electric contact 122*b* as is known in the art. According to some embodiments electrodes 120 and 130 may generate plasma inside sealed compartment 102 substantially in a dielectric breakdown discharge (DBD) mode of operation. It is noted that by disposing biomaterial 110 such as bone graft in sealed compartment 102 having a cylindrical ring shape, a large surface area of the biomaterial is exposed to plasma (compared to an exposed amount of biomaterial when disposed in a pile such as inside a plain cylinder). It is further noted that biomaterial 110 is disposed substantially between first electrode 120 and second electrodes 130, so that RF current flows near or around the biomaterial particles or in between the particles, thereby enhancing the effects on the biomaterial when plasma is activated.

For plasma generation, the portable container of the invention may be disposed in a slot of an activation device configured to generate electric power suitable to generate plasma in the sealed compartment of the portable container, as is further described and explained below.

Figure 5A:
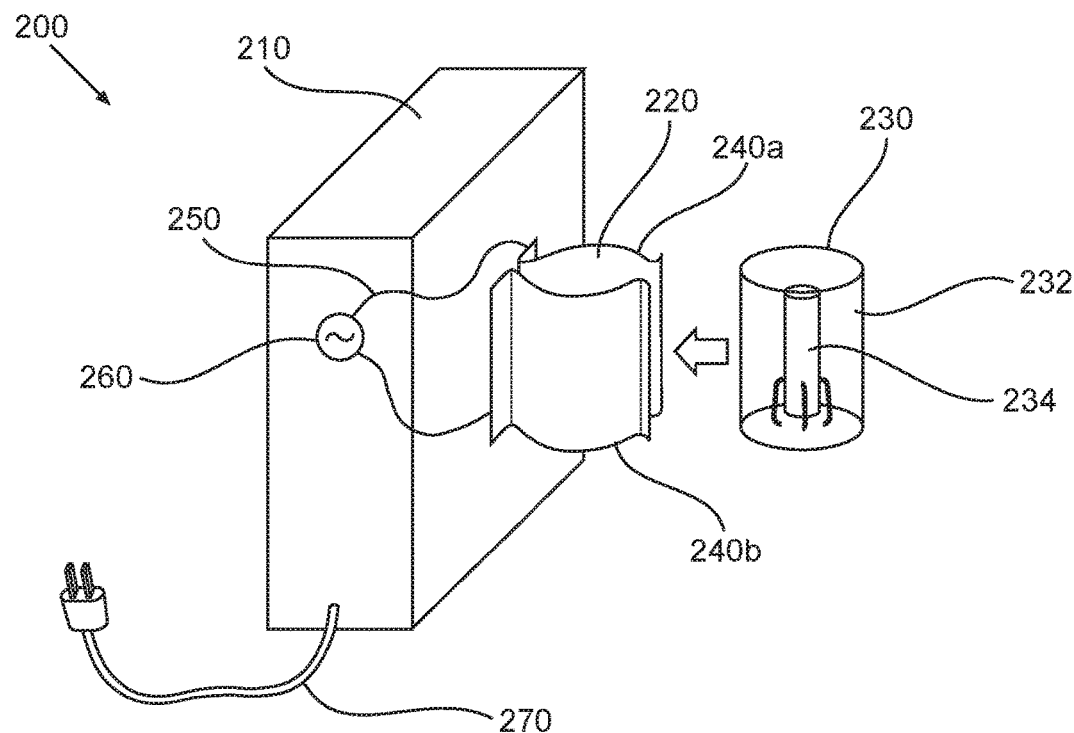
FIG. 5A schematically depicts an embodiment of an apparatus for plasma treatment of an implant prior to installing the implant in a live subject.

FIG. 5A depicts an embodiment of an apparatus 200 for plasma treatment of an implant, (implant—including an artificial implant, graft or biomaterial) prior to installing the implant in a live subject. Apparatus 200 comprises an activation device 210. The activation device comprises a slot 220 configured to receive a portable container 230. Portable container 230 comprises a sealed compartment 232 according to the teachings herein. According to some embodiments the sealed compartment contains therein a canister 234 comprising biomaterial intended to be plasma treated and then installed or used in a live subject. According to some embodiments sealed compartment 232 may contain an artificial implant 236 as depicted schematically in FIG. 5B. The sealed compartment is configured to be opened, thereby enabling removing the implant (artificial implant or graft) from the portable container when desired. Portable container 230 may comprise an electrode or electrodes configured to apply a plasma-generating EM field when coupled to a suitable EM power source, as described above for portable containers 10, 50 and 100. According to some embodiments portable container 230 does not include electrodes and plasma is generated in sealed compartment 232 thereof using external electrodes, as described herein.

Slot 220 comprises two flexible clips 240*a* and 240*b* positioned opposed to one another being thereby configured to hold a portable container in between them. According to some embodiments, flexible clips 240*a* and 240*b* are electrically conductive. According to some embodiments, flexible clips 240*a* and 240*b* are conductive and coated by an insulating layer to prevent burns or an electric shock to the user. According to some embodiments flexible clips 240*a* and 240*b* are electrically coupled with electric contacts on the portable container, such as electric contacts 38*a* and 38*b* of portable container 10. According to some embodiments the flexible clips contact electrically the electric contacts of the portable container. According to some embodiments the flexible clips are capacitively coupled to the electric contacts of the portable container Apparatus 200 further comprises an electrical circuit 250. The electrical circuit comprises an electric power source 260 configured to controllably generate an electric power (voltage and current) at a selected magnitude and frequency. The electrical circuit may receive energy from an energy source—according to some embodiments from a wall outlet through a cord 270 or according to some embodiments from a portable energy source such as an electrical battery that may be included in apparatus 200. The power source is electrically associated with the flexible clips for delivering electric power at a desired magnitude and frequency to the flexible clips for generating plasma in a sealed compartment of an attached portable container.

According to some embodiments the activation device may apply, when the portable container is disposed inside the slot, a plasma-generating electric field inside the sealed compartment of the portable container, by applying a suitable voltage between clips 240a and 240b. In some embodiments, the clips function as electrodes, configured to apply a desired field inside the sealed compartment. According to some embodiments the electrical power source of the electrical circuit is a Direct Current (DC) source, applying a DC field inside the sealed compartment. In some embodiments the electrical power source is an Alternating Current (AC) source, thereby applying an AC field inside the sealed compartment. In some embodiments the AC source generates a radio-frequency (RF) signal, for example within the range of 1 MHz and 20 MHz. According to some embodiments the portable container is similar to the portable containers of FIG. 1A or 1B or 2A or 2B or 3, in having electrodes configured for plasma generation inside the sealed compartment wherein the electrodes are electrically associated with electric contacts outside the sealed compartment. According to some embodiments the activation device may generate plasma in a portable container having such electrical contacts outside the sealed compartment by providing electric power to the electrodes inside the sealed compartment through the electrical contacts. For example, when portable container 10 is suitably placed inside slot 220, clips 240a and 240b function as electric contacts, contacting, respectively, electric contacts 38a and 38b of portable container 10. In operation electric power is provided from electric power source 260 through electric contacts 240a and 240b and through electric contacts 38a and 38b, to electrodes 26 and 42 inside the sealed compartment, thereby enabling plasma generation therein.

According to some embodiments, apparatus 200 may comprise portable container 230.

Figure 5B:
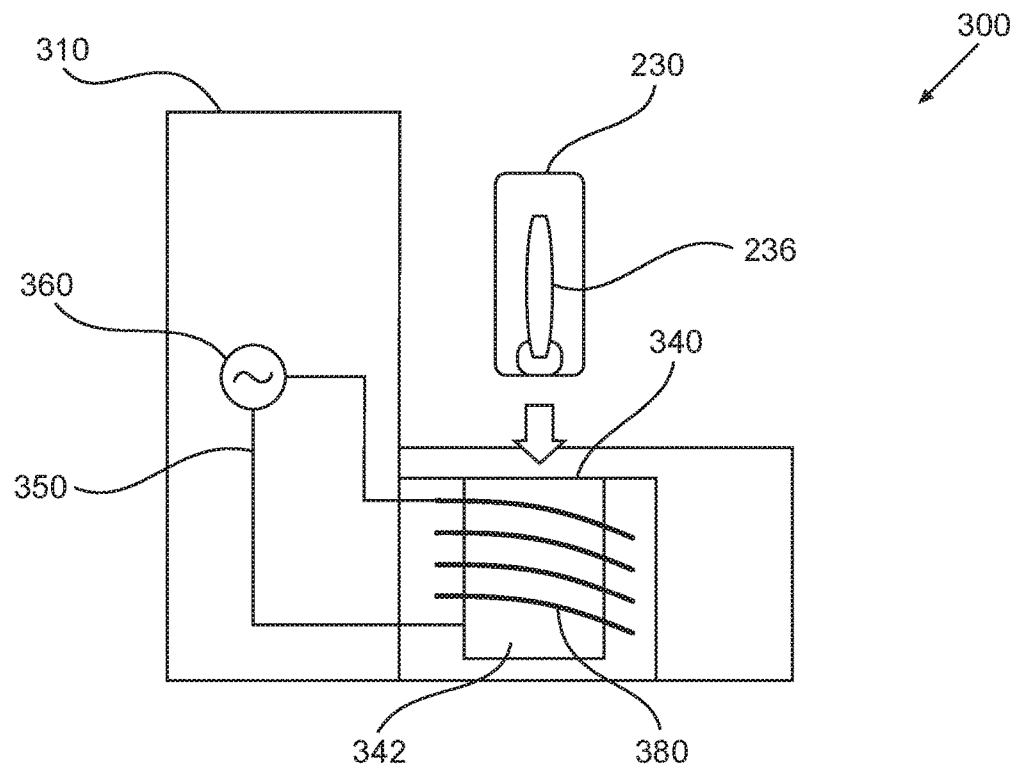
FIG. 5B schematically depicts an embodiment of another apparatus for plasma treatment of an implant prior to installing the implant in a live subject.

FIG. 5B schematically depicts an embodiment of an apparatus 300 for plasma treatment of an implant (including artificial implant or graft or biomaterial) prior to installing the implant in a live subject. Using apparatus 300, plasma may be generated inside a sealed compartment of a portable container by inducing an EM field, e.g. in an inductive coupled plasma—ICP mode, from the outside of the sealed compartment. Apparatus 300 comprises an activation device 310. The activation device comprises a slot 340 configured to receive a portable container 230. The slot 340 comprises a chamber 342 configured to receive a portable container therein.

Activation device 310 further comprises an electrical circuit 350. The electrical circuit comprises an electric power source 360 configured to controllably generate an AC electric power (voltage and current) at a selected magnitude and frequency. The electrical circuit may receive energy from an energy source—according to some embodiments from a wall outlet or according to some embodiments from a portable energy source such as an electrical battery. The electrical circuit is configured to drive an AC current through an electrode 380 electrically associated with power source 360. Electrode 380 is shaped as a coil wound around chamber 342 thereby being wound around the sealed compartment of a portable container disposed in chamber 342. According to some embodiments, plasma may be induced in the sealed compartment of a portable container disposed in chamber 342 in ICP mode. According to some embodiments, apparatus 300 may comprise portable container 230.

FIG. 6A schematically depicts an electrical configuration 400 suitable for plasma generation in a sealed compartment 410 containing an implant 416 (an artificial implant or a canister which contains biomaterial inside) of a portable container 420. An RF source 430 supplies an RF signal at a suitable magnitude and a suitable frequency for generating plasma in the sealed compartment to an electrode 440 shaped as an elongated conductor wound around the sealed compartment. The implant, or a metal segment in a canister containing biomaterial, may optionally be electrically grounded through a ground electrode 450. According to some embodiments the implant 416 is electrically floating, that is to say being electrically disconnected from a power source, and plasma is induced in sealed compartment 410 using only electrode 440 in an ICP mode of operation. According to some embodiments the implant 416 is dielectric. According to some embodiments implant 416 comprises metallic parts and dielectric parts, and the implant is supported in sealed compartment 410 so that ground electrode 450 contacts a dielectric part of the implant, and not a metallic part. According to some embodiments both ends of the conductor of electrode 440 are electrically connected to contact 460a.

According to some embodiments the RF source may be comprised in the portable container 420, rendering the portable container configured for plasma generation (inside the sealed compartment) upon receiving energy from an energy source such as a wall outlet or a portable source such as a battery. According to some embodiments the RF source may be comprised in an activation device (not shown in this Figure) generally separated from the portable container such as activation device 210 or activation device 310. In some embodiments electrode 440 may be wound around a chamber configured to receive portable container 420, as is described in FIG. 5B above. Contacts 450a (on portable container 420) and 450b (on the activation device) contact each other when the portable container is disposed in the slot of the activation device, thereby electrically grounding the implant. According to some embodiments the portable container comprises electrode 440 being wound around the sealed compartment thereof, and contacts 460a (on portable container 420) and 460b (on the activation device) also contact each other when the portable container is disposed in the slot of the activation device, thereby enabling providing plasma generating EM signal from the RF source to electrode 440.

FIG. 6B schematically depicts an electrical configuration 500 suitable for plasma generation in a sealed compartment 510 containing an implant 416 (e.g. an artificial implant or a canister which contains biomaterial inside) of a portable container 520. Plasma generation in electrical configuration 500 is achieved using a first electrode 540 shaped as an elongated conductor wound around the sealed compartment, and a second electrode 550 shaped as an elongated conductor wound around the sealed compartment. First electrode 540 receives a first voltage, typically from a power source 530, and second electrode 550 receives a second voltage, different from the first voltage, and is typically grounded. Plasma may be generated in a Dielectric Barrier Discharge (DBD) mode of operation as a dielectric barrier (the walls of the sealed compartment) separate between at least one of the electrodes and the region where plasma is generated. Any of first electrode 540 and second electrode 550 may be coated by an insulating material e.g. to prevent arcing between them. Contacts 560a, 560b, 570a and 570b may function as described above to enable the portable container to include the RF source for providing the plasma-generation EM field according to some embodiments or alternatively to be electrically associated with an activation device for plasma generation.

FIG. 6C schematically depicts an electrical configuration 600 suitable for plasma generation in a sealed compartment 510 containing an implant 416 of a portable container 520. Electrical configuration 600 is different from electrical configuration 500 in that a first electrode 640 is wound around the sealed compartment several wounds, and a second electrode 650 is wound around the sealed compartment several wounds, and the wounds of first electrode 640 and second electrode 650 are interleaved, to generate plasma uniformly. Any of first electrode 640 and second electrode 650 may be coated by an insulating material e.g. to prevent arcing between them.

According to an aspect of some embodiments there is provided a portable container for handling an implant, the portable container comprising an external capsule and an internal capsule, wherein the internal capsule is contained within the external capsule. The internal capsule defines an internal compartment, and the internal compartment houses an implant therein. The internal capsule is microbially sealed, thereby maintaining sterility of the implant. Being "microbially sealed" herein means that microbial organisms may not penetrate into the microbially sealed internal capsule, wherein microbial organisms may include any form of viruses, prokaryotic cells or eukaryotic cells, including fungi and bacteria. In some embodiments the internal capsule may be substantially sealed, thereby substantially preventing penetration or escape of fluid into or out from the internal capsule, and thereby substantially maintaining composition and pressure of a fluid stored inside the internal capsule. In some embodiments the internal capsule is microbially sealed using a suitable filter that allows passage of fluid molecules therethrough (e.g. gaseous molecules) but prevents passage of microbial organisms therethrough. In some embodiments the internal capsule may contain a fluid having substantially the same pressure and composition as the pressure and composition, respectively, of a fluid in which the internal capsule is immersed. At least one of the external capsule and the internal capsule may function as a sealed compartment of the portable container. That is to say, at least one of the external capsule and the internal capsule contains a fluid having a pre-defined composition and pressure, the fluid being adapted and configured to be ionized and excited to plasma when subject to a suitable EM field. The sealed compartment is sealed from ambient atmosphere, that is to say the sealed compartment is configured to prevent penetration or escape of fluid into or out from the sealed compartment, being thereby configured to maintain composition and pressure of a fluid stored inside the sealed compartment.

The external capsule is further configured and dimensioned for freely releasing the internal capsule when the external capsule is opened. Being configured for freely releasing the internal capsule herein means that following opening the external capsule, the internal capsule may be extracted and removed from the opened external capsule without touching the internal capsule. For example, the external capsule may have an opening that may be sealed by a cap. A user may open the external capsule by removing the cap and then freely releasing the internal capsule from the external capsule by holding the external capsule so that the opening faces downwards, thereby letting the internal capsule fall down and out from the external capsule through the opening. In some embodiments the internal capsule may be held tight inside the external capsule, whereas a releasing mechanism operated by the user may be used to release the internal capsule from the holding, thereby freely releasing the internal capsule from the external capsule.

The internal compartment is configured to enable plasma treatment of the implant there inside. The internal capsule contains a first ionizable fluid, which is exciteable to plasma when subjected to a suitable exciting electromagnetic field. Various configurations of the internal capsule and the external capsule, and related composition and pressure of the first ionizable fluid are envisaged, such that plasma excitation may be obtained within the internal capsule. Some exemplary embodiments are described in more detail herein below.

For use, according to some embodiments, the portable container may be sealed, with the implant there inside, in a manufacturing site, wherein an implant is disposed inside the internal capsule and the internal capsule, containing an ionizable fluid (liquid or gas) is disposed inside the external capsule. The implant is sealed by at least one of the external capsule and the internal capsule, such sealing of the implant may be carried out after the manufacturing process of the implant, optionally at the manufacturing site. According to some embodiments such sealing may be carried out prior to storing the implant or prior to shipping the implant or prior to distributing the implant to users.

The implant may be sterilized at the implant manufacturing site before disposing into the internal capsule or after disposing into the internal capsule (e.g. using gamma radiation). Alternatively or additionally, the implant may be sterilized by the plasma treatment inside the portable container according to the teachings herein, prior to use. The implant inside the portable container may then be stored for a few days or weeks or for months or even for years—and then may be taken for use. When in a medical treatment site, the portable container may be activated for generating plasma at least in the internal capsule. For example, the portable container may be placed in a dedicated slot of an activation device, the activation device being configured and operable for generating an EM field suitable for exciting plasma in the internal capsule. The activation device may include for example an RF generator and an amplifier configured for generating high voltage—e.g. above 100V or even above 1 KV. The generated RF high voltage may be supplied to electrodes that generate the plasma activating field in the portable container.

Plasma may be generated by turning on the electric circuit, resulting in treating the implant inside the internal capsule, thereby preparing the implant for installment. Then plasma generation may be stopped. If for any reason the external capsule is not opened after the plasma generation, plasma generation can be repeated at a later occasion, e.g. by turning on the electric circuit again, as described above.

The external capsule may be made in some embodiment of a dielectric material such as plastic or glass. According to some embodiments the external capsule may comprise a first metallic segment, providing electric conductance from the outside of the external capsule to the inside thereof. According to some embodiments the external capsule may include a feed through—optionally a sealed feed through—for providing such electric conductance from the outside of the external capsule to the inside thereof. According to some embodiments, a non-conducting implant may be plasma-treated in a portable container of the invention. For example, an implant made of a dielectric material such as polymer material or ceramic, and void of metal, may be plasma treated according to the teachings herein. According to some embodiments an implant made of electrically isolating material may be disposed in the internal capsule, and a single electrode enveloping the implant may generate plasma e.g. in an ICP mode of operation. According to some embodiments the electrode is isolated from the excited medium (the fluid which is excited to plasma) by an isolative layer. According to some embodiments the single electrode may be disposed outside the internal capsule, being thereby isolated from the ionizable fluid inside the internal capsule by the internal capsule itself. According to some embodiments two electrodes may be employed to induce a plasma generating EM in a region substantially between the electrodes. According to some embodiments two electrodes, isolated from the ionizable fluid in which the implant is immersed may be employed to induce a plasma generating EM field, e.g. in a DBD mode of operation. According to some embodiments the two electrodes may be disposed outside the internal capsule, being thereby isolated from the ionizable fluid inside the internal capsule by the internal capsule itself. According to some embodiments a single electrode or two electrodes inside the external capsule may be contacted from the outside of the external capsule through metallic segments or feed-throughs or sealed feed-throughs in the external capsule as described above.

According to some embodiments a metallic segment in the external capsule may be used as an electrode for generating the plasma activating field, or for contacting such an electrode inside the external capsule. In some embodiments the external capsule may comprise further a second metallic segment, electrically isolated from the first metallic segment described above, the second metallic segment being used as a second electrode for the plasma generating field. In a particular exemplary embodiment a first metallic segment of the external capsule may be in electrical contact with a metallic implant whereas a second metallic segment is formed as a cylinder positioned outside the internal capsule and substantially surrounding the implant therein. An EM field (e.g. RF field) may then be supplied to the two metallic segments, thus generating a plasma exciting field between the implant and the cylindrical electrode, in the ionizable medium within the internal capsule.

The internal capsule may be made from a dielectric material such as plastic or glass. In some embodiments the internal capsule may have a metallic segment for providing electric conductance from the outside of the internal capsule to the inside thereof. In some embodiments the metallic segment of the internal capsule may electrically contact a metallic implant in a point or a region of the implant which does not require surface treatment by the plasma. In some particular embodiments, the internal capsule may be sealed (or microbially sealed, as described above) using a metallic cap having an implant holder on the inside surface thereof for holding the implant. In some embodiments the implant (e.g. a dental implant) may be mechanically attached to a metallic insertion driver having a cross section fitting to an opening of the internal capsule. The internal capsule may be sealed by inserting the implant to the internal capsule whereas the opening thereof is sealed by the insertion driver, part of the insertion driver left outside the internal capsule and used as an electric contact to the implant.

In some embodiments the internal capsule is made of a dielectric material at least in regions thereof facing surfaces of the implant requiring plasma treatment. In other words, when the implant is used as one of the electrodes for the plasma generating field, the other electrode is separated from the implant by a dielectric barrier, for properly establishing a DBD mode of operation.

Thus, according to some embodiment the fluid in the external capsule may be configured to be ionized, substantially similarly to the fluid inside the internal capsule, whereas one electrode of the plasma generating field is positioned externally to the external capsule. Accordingly, the fluid in the external capsule may be gas, comprising a predefined gaseous composition at a pre-defined pressure. According to some embodiments the fluid comprises a liquid having a pre-defined composition, such as a saline composition at a pre-defined concentration. According to other embodiments an electrode is disposed inside the external capsule externally to the internal capsule. For example an electrode may be embodied by a metallic coating on the external surface of the internal capsule (being electrically isolated from the implant and from any electric conductor which is in electrical contact with the implant). Plasma is generated in such embodiments only within the internal capsule, and the atmosphere inside the external capsule may not need to be ionizable.

Figure 7A:
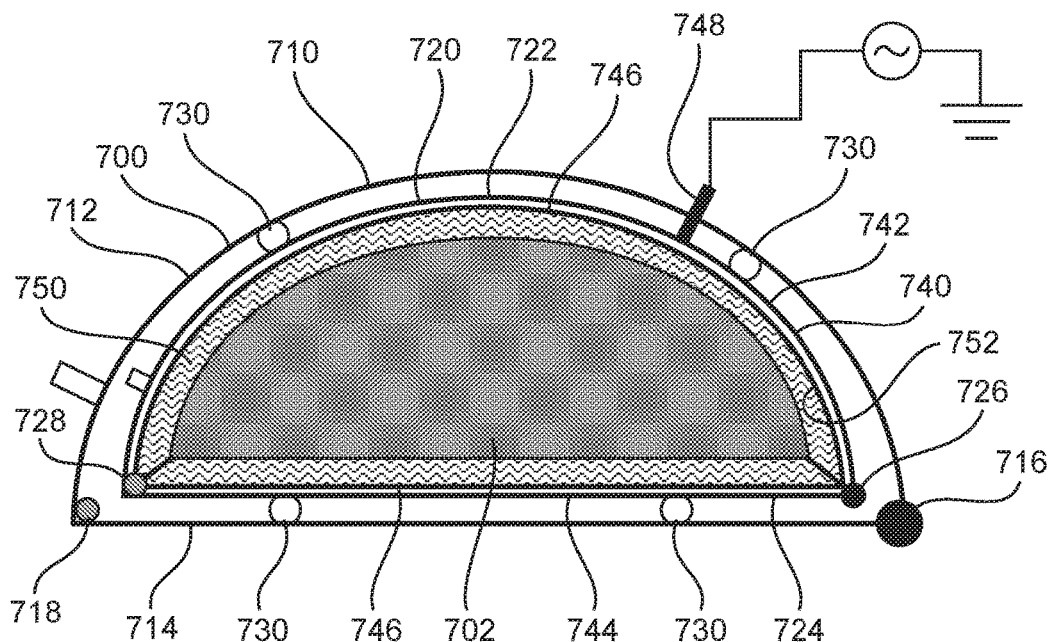
FIG. 7A schematically depicts an embodiment of a portable container having an internal capsule, an external capsule and a single electrode, for handling and plasma-treating a breast implant.

FIG. 7A schematically depicts an embodiment of a portable container 700 for handling a breast implant 702 according to the teachings herein. Portable container 700 is shaped as a hollow dome and dimensioned to contain therein a breast implant such as a breast implant made as a soft lump such as elastomer silicone shell filled with silicone gel or saline composition. Portable container 700 comprises an external capsule 710, schematically depicted in FIG. 7A in a closed state, having a vault cover 712 on top of a flat base 714. External capsule 710 is configured to be pivotally opened and closed by lifting and lowering vault cover 712 relative to flat base 714 around a pivot 716. Other embodiments, employing different techniques of closing external capsule 710, as are known in the art—for example screwing vault cover 712 onto flat base 714—are contemplated. According to some embodiments external capsule 710 may be sealingly closed using a seal 718 between vault cover 712 and flat base 714. When sealingly closed, external capsule 710 is configured to maintain inside a fluid—liquid or gas—in a predefined composition and pressure, sealed from external atmosphere.

Portable container 700 further comprises a sealed compartment 720, embodied by an internal capsule contained within external capsule 710, schematically depicted in FIG. 7A in a closed state. Sealed compartment 720 comprises a compartment vault 722 on top of a compartment base 724. Sealed compartment 720 is configured to be pivotally opened and closed by lifting and lowering compartment vault 722 relative to compartment base 724 around a compartment pivot 726. Other embodiments, employing different techniques of closing sealed compartment 720, as are known in the art—for example screwing compartment vault 722 onto compartment base 724—are contemplated. Sealed compartment 720 may be sealingly closed, sealing being achieved using a compartment seal 728 between compartment vault 722 and compartment base 724. When sealingly closed, sealed compartment 720 is configured to maintain inside a fluid—liquid or gas—in a predefined composition and pressure, sealed from the fluid outside of sealed compartment 720. Sealed compartment 720 is optionally supported and stabilized inside external capsule 710 by bumpers 730 positioned between external capsule 710 and sealed compartment 720.

Portable container 700 is configured to enable removing implant 702 from sealed compartment following a plasma treatment, in a sterile surrounding, into a sterile tray or sterile hands or a sterile vessel, and while maintaining sterility of the implant. Accordingly, sealed compartment 720 is dimensioned (when in closed state) so as to insert freely into external capsule 710 (the external capsule being open), and to release freely therefrom. In other words, sealed compartment 720 may be disposed inside external capsule 710 and when external capsule 710 is closed, sealed compartment 720 is held tight, being supported optionally by bumpers 730. When external capsule 710 is opened, sealed compartment 720 may be freely released from external capsule 710, e.g. by turning external capsule 710 upside down, thereby causing sealed compartment 720 to slide freely downwards and fall down from external capsule 710 optionally onto a sterile tray or the like, as explained above without touching sealed compartment 720, and thus without endangering the sterility thereof.

Compartment vault 722 and compartment base 724 comprise an enveloping electrode 740, having a top section 742 on compartment vault 722 and a bottom section 744 on compartment base 724, the top section and the bottom section being in electrical contact with one another. Enveloping electrode 740 is electrically isolated from the fluid inside sealed compartment 720 by an insulating layer 746. Consequently, plasma may be generated inside sealed compartment 720 using enveloping electrode 740 in DBD mode of operation. RF power for inducing a plasma generating EM field may be supplied to enveloping electrode 720 using a sealed feed-through 748 in external capsule 710.

Portable container 700 further comprises an implant support agent 750, disposed between the implant and a compartment internal surface 752. Implant support agent 750 is made of a dielectric material and configured to stabilize breast implant 702 in place inside sealed compartment 720, substantially between compartment vault 722 and compartment base 724 when sealed compartment 720 is closed Implant support agent 750 is further configured to contact the implant over only a small portion of the implant surface, thereby leaving a large portion of the implant's surface exposed to plasma treatment. According to some embodiments implant support agent 750 may comprise a sheet or sheets of an electrically insulating, porous and optionally flexible material such as a sponge. The size of the pores in the implant support agent 750 are configured to be large enough to allow plasma ignition within the pores during operation, and to be small enough so that the walls between the pores provide effective mechanical support to the implant. According to some embodiments pores typical dimensions should be smaller than about 2 cm and larger than about 1 mm According to some embodiments implant support agent may comprise a wavy or undulating sheet or sheets of an electrically insulating material. According to some embodiments the wavy or undulating sheet may be shaped to have craters such as in a muffin-tin or an eggcarton. According to some embodiments the craters may be punctured. The wavy or undulating sheet may be configured to have tips or ridges along the surface contacting the implant, so as to minimize the portion of the implant surface which is obscured by the implant support agent, thus not exposed to plasma treatment. According to some embodiments the craters are dimensioned generally similarly to the pores as described above, having dimensions between about 1 mm and about 2 cm Implant support agent 750 may have a uniform thickness thus establishing a uniform distance between the implant and the electrode, thereby enabling a uniform current density between the electrode and the implant during plasma activation. According to some embodiments the implant support agent may have a thickness between about 0.5 mm and about 2 cm. According to some embodiments the implant support agent may have a thickness in the range between about 1 mm and about 1 cm, for example a thickness of about 2 mm, or a thickness of about 5 mm or a thickness of about 8 mm.

The sealed compartment is configured to contain an ionizable fluid—liquid or gas—so that the implant support agent and the implant are immersed therein. The fluid inside the sealed compartment is configured to be excited to plasma when subject to a plasma exciting EM field, as is described in detail above e.g. regarding the sealed compartments of portable containers 10, 50 and 100. In use, that is to say, when plasma is excited in the sealed compartment, current flows between enveloping electrode 740 and implant 702 and consequently plasma is excited in the space there between.

Figure 7B:
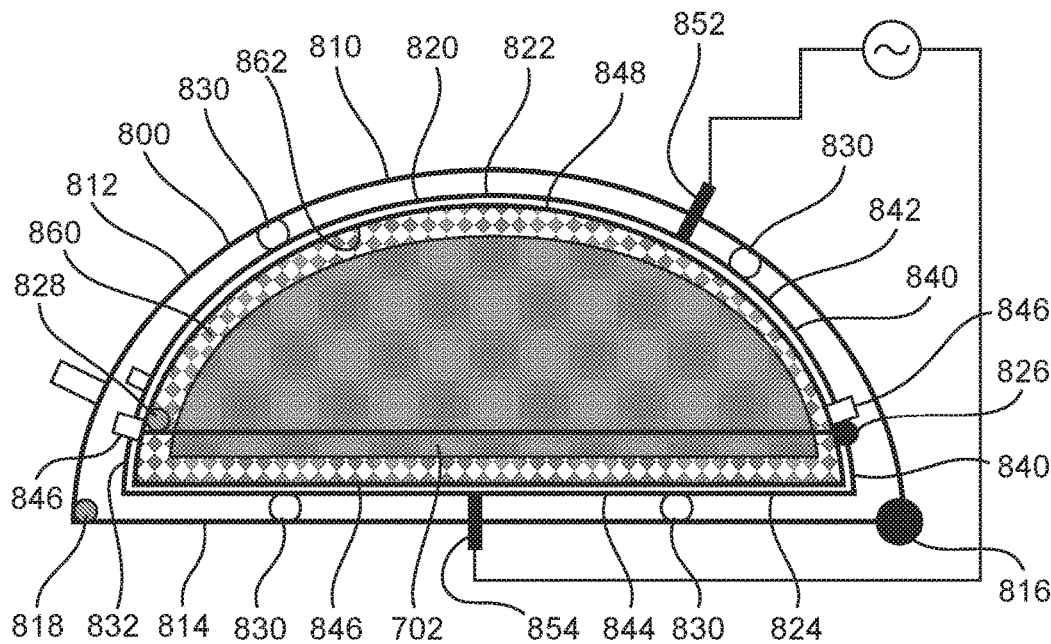
FIG. 7B schematically depicts an embodiment of a portable container having an internal capsule, an external capsule and a two electrodes, for handling and plasma-treating a breast implant.

FIG. 7B schematically depicts an embodiment of a portable container 800 for handling a breast implant 702 according to the teachings herein. Portable container 800 is different from portable container 700 by having two electrodes for applying the plasma-activating EM field, as is described below. Portable container 800 is shaped as a hollow dome and dimensioned to contain therein a breast implant as described above. Portable container 800 comprises an external capsule 810, schematically depicted in FIG. 7B in a closed state, having a vault cover 812 on top of a base 814. External capsule 810 is configured to be pivotally opened and closed by lifting and lowering vault cover 812 relative to base 814 around a pivot 816. Other embodiments, employing different techniques of closing external capsule 810, as are known in the art—for example screwing vault cover 812 onto base 814—are contemplated. According to some embodiments external capsule 810 may be sealingly closed using a seal 818 between vault cover 812 and base 814. When sealingly closed, external capsule 810 is configured to maintain inside a fluid—liquid or gas—in a predefined composition and pressure, sealed from external atmosphere.

Portable container 800 further comprises a sealed compartment 820, embodied by an internal capsule contained within external capsule 810, schematically depicted in FIG. 7B in a closed state. Sealed compartment 820 comprises a compartment vault 822 on top of a compartment base 824. Sealed compartment 820 is configured to be pivotally opened and closed by lifting and lowering compartment vault 822 relative to compartment base 824 around a compartment pivot 826. Other embodiments, employing different techniques of closing sealed compartment 820, as are known in the art—for example screwing compartment vault 822 onto compartment base 824—are contemplated. Sealed compartment 820 may be sealingly closed using a compartment seal 828 between compartment vault 822 and compartment base 824. When sealingly closed, sealed compartment 820 is configured to maintain inside a fluid—liquid or gas—in a predefined composition and pressure, sealed from the fluid outside of sealed compartment 820. Sealed compartment 820 is supported and stabilized inside external capsule 810 by bumpers 830 positioned between external capsule 810 and sealed compartment 820. It is noted that compartment base 824 has a rim 832 around the circumference thereof, extending upwards into the dome portion of sealed compartment 820, and consequently compartment vault 822 extends over only a segment of the dome portion of the sealed compartment.

Sealed compartment 820—when in a closed state—is configured to insert freely into external capsule 810, and to release freely therefrom, substantially as explained above regarding portable container 700.

Portable container 800 comprises an electrode pair 840, having a top electrode 842 extending over compartment vault 822, and a bottom electrode 844 extending over compartment base 824. Top electrode 842 is electrically isolated from bottom electrode 844. Isolator 846 extends along edges of top electrode 842 and bottom electrode 844 to ensure electrical isolation between the two electrodes. Top electrode 842 has an equal are to an area of bottom electrode 844 so that in operation, a current density through the two electrodes is the same. Rim 832 is sized and dimensioned so that the area of bottom electrode 844 is equal to the area of top electrode 842.

Electrode pair 840 is electrically isolated from the fluid inside sealed compartment 820 by an insulating layer 848. Consequently, plasma may be generated inside sealed compartment 820 using Electrode pair 840 in DBD mode of operation. RF power for inducing a plasma generating EM field may be supplied to top electrode 842 and to bottom electrode 844 using a first sealed feed-through 852 and second sealed feed-through 854, respectively, in external capsule 810.

Portable container 800 further comprises an implant support agent 860, disposed between the implant and a compartment internal surface 862. Implant support agent 860 has substantially similar materials and characteristics to those of implant support agent 750

Sealed compartment 820 is configured to contain an ionizable fluid—liquid or gas—so that the implant support agent and the implant are immersed therein. The fluid inside the sealed compartment is configured to be excited to plasma when subject to a plasma exciting EM field, as is described in detail above e.g. regarding the sealed compartments of portable containers 10, 50, 100 and 700. In use, that is to say when plasma is excited in the sealed compartment, current flows between top electrode 842 and implant 802 and between implant 802 and bottom electrode 844, and consequently plasma is excited in the space there between.

Figure 8A:
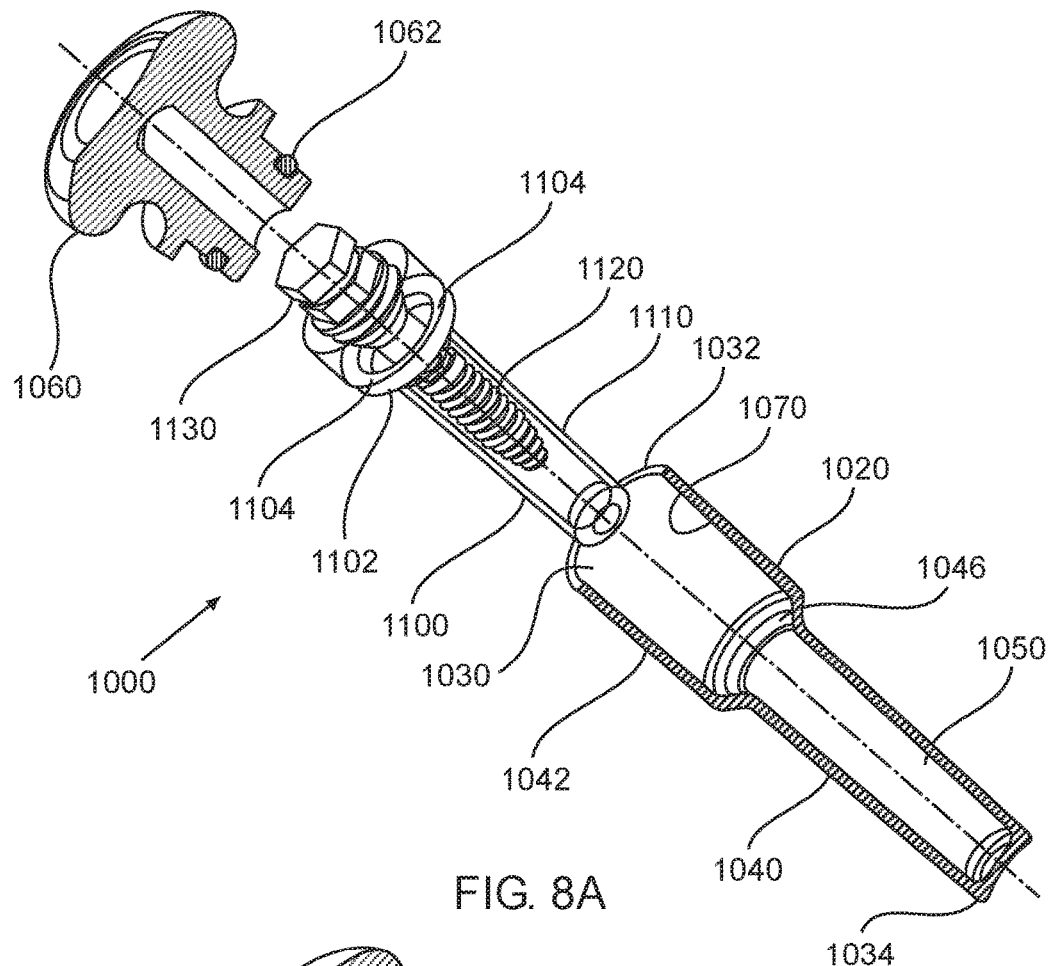
FIG. 8A schematically depicts an embodiment of a portable container having an internal capsule and an external capsule for handling and plasma-treating a dental implant, in a semi-exploded view.
Figure 8B:
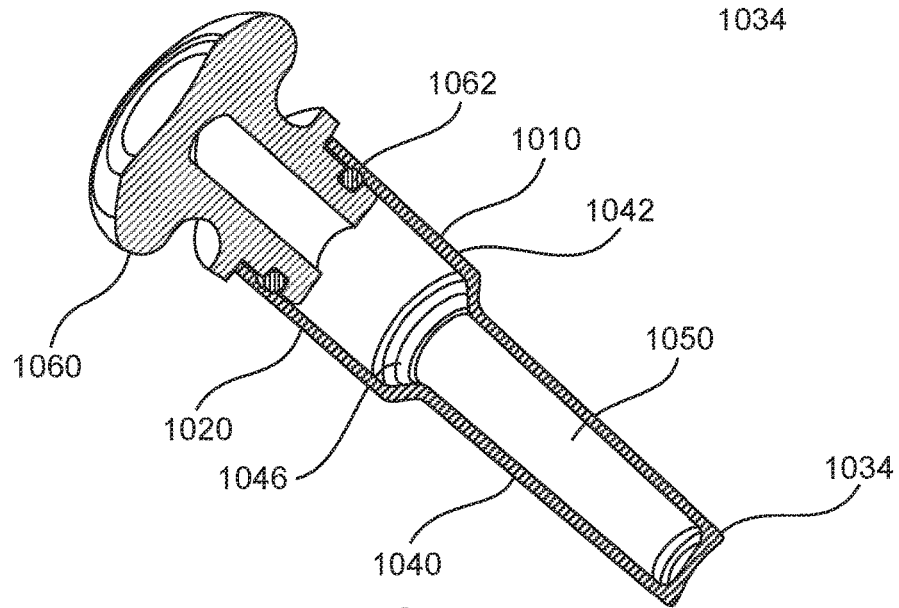
FIG. 8B schematically depicts the sealed compartment of the portable container of FIG. 8A, in a closed state in a cross-section view.

FIG. 8A schematically depicts an embodiment of a portable container 1000 for handling a dental implant, in a semi-exploded view. Portable container 1000 comprises a sealed compartment 1010, depicted in a closed state in a cross-section view in FIG. 8B. Sealed compartment 1010 comprises an external capsule 1020 having a shape of an elongated hollow vessel having an opening 1030 at a top end 1032 thereof and a bottom end 1034 thereof being closed and sealed. In some embodiments external capsule 1020 is made of a dielectric material, possibly transparent, such as a polymeric material (e.g. Perspex®) or glass.

External capsule 1020 has a narrow bottom part 1040 and a wide top part 1042, the narrow part 1040 and the wide part 1042 being separated by a dividing shoulder 1046. Dividing shoulder 1046 defines a plasma excitation region 1050 within narrow bottom part 1040, as is further detailed and explained below.

Sealed compartment 1010 further comprises a metallic cap 1060 configured and dimensioned to insert into opening 1030 thereby sealing sealed compartment 1010. Cap 1060 comprises a seal 1062 configured to fit to an internal surface 1070 of external capsule 1020 proximal to opening 1030, thereby sealing sealed compartment 1010 when cap 1060 is suitably inserted through opening 1030 to external capsule 1020. According to some embodiments seal 1062 may be embodied by an O-ring made for example of rubber. According to some embodiments metallic cap 1060 and external capsule 1020 near opening 1030 may be threaded, and metallic cap 1060 may insert into opening 1030 by screwing. According to some embodiments seal 1062 may be embodied by a flat seal. The flat seal may be made form a suitable material as is known in the art. In some embodiments the flat seal may be made of plastic. In some embodiments the flat seal may be made of metal, e.g. soft metal.

Portable container 1000 further comprises a microbially sealed internal capsule 1100 configured for housing a dental implant 1120 attached to an insertion driver 1130. External capsule 1020 is dimensioned to house internal capsule 1100 so that when internal capsule 1100 with implant 1120 inside is suitably disposed inside external capsule 1020, implant 1120 is substantially within plasma excitation region 1050 of external capsule 1020. Internal capsule 1100 is made of a dielectric material, possibly transparent, such as a polymeric material (e.g. Perspex®) or glass. A dielectric ring 1102 is positioned around an outer surface 1110 of internal capsule 1100 so as to dimensionally match dividing shoulder 1046. When internal capsule 1100 is suitably disposed inside external capsule 1020, dielectric ring 1102 is pressed downwards towards dividing shoulder 1046 thereby forming a contiguous dielectric barrier (composed from the narrow bottom part 1040 of external capsule 1020, the dielectric ring 1102 and the internal capsule 1100), that dielectrically limits the plasma to the plasma excitation region 1050. In other words, when a plasma excitation field is applied between an external electrode (e.g. in a form of a cylinder arranged around narrow bottom part 1040, not shown in this Figure) and dental implant 1120, dielectric ring 1102 prevents excitation of plasma in a region above the ring, for example in the wide top part 1042 of external capsule 1020. Internal capsule 1100 comprises equalizing slots 1104 on the outer surface 1110 of internal capsule 1100, underneath dielectric ring 1102, extending from below the dielectric ring to above the dielectric ring. Equalizing slots 1104 are configured to ensure fluid communication between plasma excitation region 1050 below dividing shoulder 1046 and dielectric ring 1102 to the space inside wide part 1042 above dielectric ring 1102, when the internal capsule is held inside external capsule 1020. Thus, pressure equilibrium is always maintained below and above dielectric ring 1102.

In use, sealed compartment 1010 may be sealed with internal capsule 1100 and dental implant 1120 inside, internal capsule 1100 comprising a gaseous composition configured to allow plasma ignition and plasma maintaining by an electromagnetic field. According to some embodiments internal capsule 1100 contains a gaseous atmosphere at a low pressure—e.g. below 1 Atmosphere or even below 0.02 Atmosphere or even below 0.01 Atmosphere. The pressure and composition of the gaseous atmosphere inside internal capsule 1100 may be substantially identical to the pressure and composition of the gaseous atmosphere within external capsule 1020. According to some embodiments the pressure and composition inside internal 1100 capsule is different from the pressure and composition in the space between internal capsule 1100 and external capsule 1020. According to some embodiments, an electric filed may be applied between an external electrode (such as cylindrical electrode around external capsule 1020) and the implant, and plasma may be generated inside internal capsule 1100 but not in the space between internal capsule 1100 and external capsule 1020.

When external capsule 1020 is closed and sealed by cap 1060, external pressure of room atmosphere (being greater than the pressure inside the external capsule) thus tends to press cap 1060 towards external capsule 1020. Cap 1060 is dimensioned to press onto insertion driver 1030, thus forming an electric contact with dental implant 1120 through insertion driver 1130. Further, through insertion driver 1130 and dental implant 1120, cap 1060 presses internal capsule 1100 and dielectric ring 1102 onto dividing shoulder 1046, thus forming the dielectric barrier of plasma excitation region 1050, as described above. It is noted that when cap 1060 is opened and the space above dielectric ring 1102 is ventilated (reaching atmospheric pressure), the plasma excitation region 1050 is ventilated also through equalizing slots 1104, thereby removing any pressure difference between below and above the dielectric ring.

Internal capsule 1100 and dielectric ring 1102 are dimensioned so as to insert freely into external capsule 1020, and to release freely therefrom. In other words, internal capsule 1120 is disposed inside external capsule 1020 substantially without friction between the two capsules, and when sealed compartment 1010 is closed and sealed by cap 1060, internal capsule 1100 is held tight, pressed between cap 1060 and dividing shoulder 1046. Thus, when cap 1060 is opened, internal capsule 1100 may be freely released from external capsule 1020, e.g. by turning external capsule 1020 upside down, opening 1030 facing downwards, thereby causing internal capsule 1100 to slide freely downwards and fall down and out from external capsule 1020. The ventilation of plasma excitation region 1050 when cap 1060 is opened through equalizing slots 1104 removes any pressure difference between both sides of the dielectric ring 1102, thereby preventing a net force that might apply to maintain internal capsule 1100 inside external capsule 1020. It is noted that various alternatives to equalizing slots 1104 are contemplated to provide ventilation between bottom narrow part 1040 and top wide part 1042 when internal capsule is disposed inside external capsule 1020. Various embodiments of channels providing fluid communication between bottom narrow part 1040 and top wide part 1042, as are known by those skilled in the art, may be employed to provide such ventilation.

FIG. 9A schematically depicts dental implant 1120 attached to insertion driver 1130 and a cross-section of internal capsule 1100 in a semi exploded view. FIG. 9B schematically depicts dental implant 1120 and insertion driver 1130 in an exploded view. Internal capsule 1100 is formed as an elongated hollow vessel with a top capsule opening 1140 and a sealed capsule bottom 1142. Internal capsule 1100 defines an internal compartment 1150, having an internal surface 1152, the internal compartment 1150 substantially housing dental implant 1120. Internal compartment 1150 comprises a support shoulder 1154 on internal surface 1152, for supporting insertion driver 1130 (attached to dental implant 1120). A sealing ring 1160 is attached around insertion driver 1130, so that when dental implant 1120 is suitably placed inside internal capsule 1100, sealing ring 1160 is supported on support shoulder 1154 thereby sealing the space inside internal capsule 1100 below support shoulder 1154, housing dental implant 1120. It is noted that when dental implant 1120 is sealed inside internal capsule 1100 e.g. in the dental implant manufacturing site or prior to shipment of the implant, the pressure inside internal capsule 1100 may be below 1At as described above. When internal capsule 1100 together with dental implant 1120 is released from external capsule 1020 following a plasma treatment as described above, room pressure around internal capsule 1100 generates pressure onto insertion driver 1130 towards internal capsule 1100, thereby maintaining the sealing between sealing ring 1160 and support shoulder 1154. When dental implant 1120 is to be installed, a surgeon or an assistant or a care giver may pull out insertion driver 1130 together with dental implant 1120 attached thereto from internal capsule 1100, e.g. by hand, overcoming the atmospheric pressure, and continue with preparing the dental implant for installing.

Figure 10:
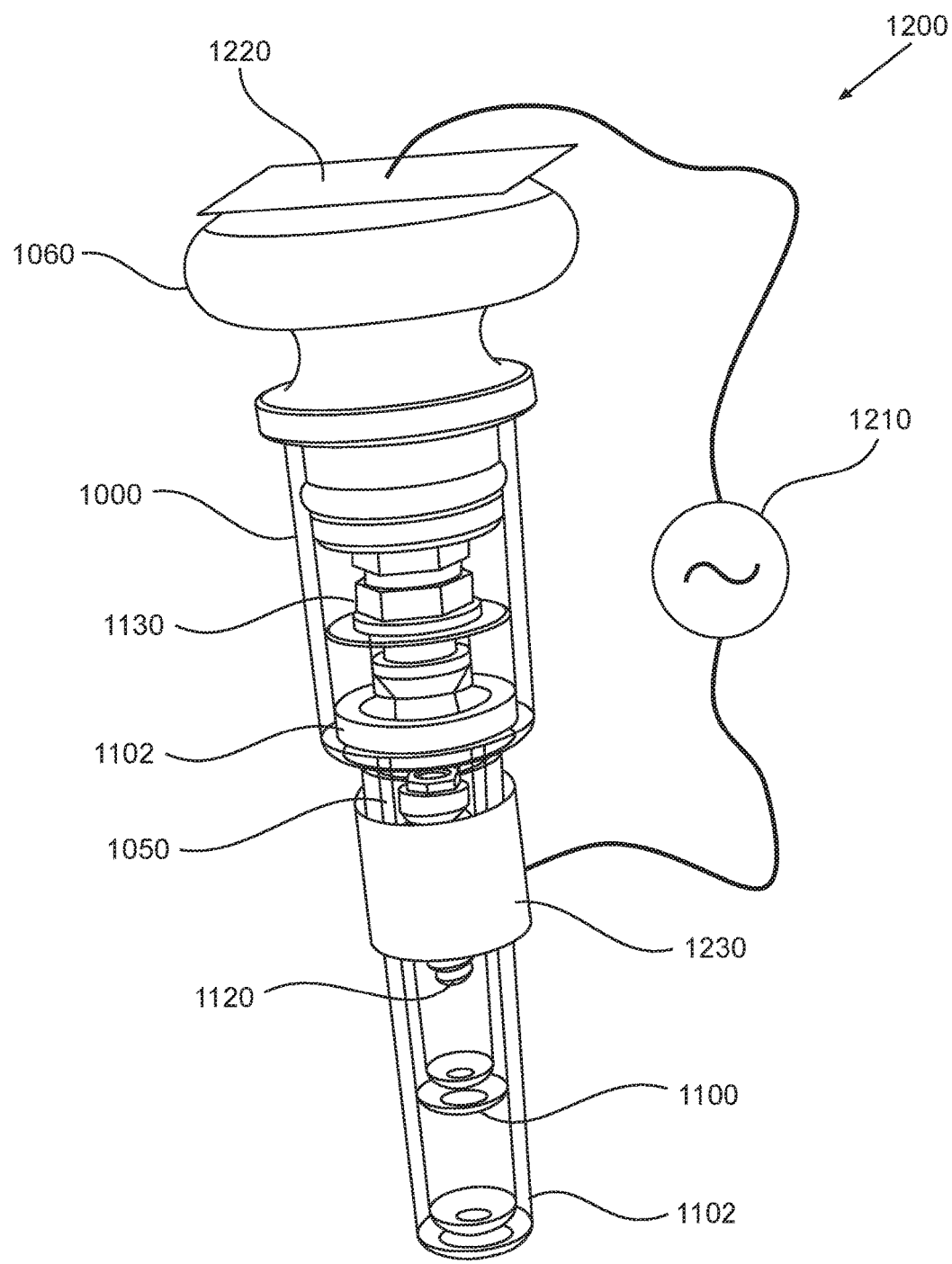
FIG. 10 schematically depicts an embodiment of an electric circuit for applying a plasma activating electromagnetic field in the sealed compartment of the portable container of FIGS. 8 and 9.

FIG. 10 schematically depicts an embodiment of an electric circuit 1200 for applying a plasma activating EM field in portable container 1000. A RF power source 1210 is electrically associated with a cap electrode 1220 and with a cylindrical electrode 1230. Cap electrode 1220 is electrically contacting metal cap 1060, thereby having electrical contact with dental implant 1120 through insertion driver 1130. Cylindrical electrode 1230 is wrapped around plasma excitation zone 1050 of external capsule 1020. Electric circuit 1200 may be embodied for example within an activation device (not shown in this Figure) sited in a clinic or a care-giving center for use prior to installing the implant. The activation device may have a slot configured for accepting portable container 1000 therein, so that cylindrical electrode 1230 and cap electrode 1220 are electrically associated with the portable container as schematically depicted in FIG. 10. According to some embodiments portable container 1000 may comprise a cylindrical electrode wrapped around plasma excitation zone 1050 of external capsule 1020—e.g. coated onto the outer surface of external capsule 1020—and the activation device may have an electrode configured to electrically contact the coated region thereby providing electric power to the cylindrical electrode for establishing the plasma generating field.

Upon activation of electric circuit 1200, a plasma activation field is established substantially between dental implant 1120 and cylindrical electrode 1230. The plasma activation field overcomes the dielectric barrier formed by the external capsule 1020 and by the internal capsule 1100 in the plasma generation region 1050, thereby generating plasma in the gaseous atmosphere within the internal capsule and possibly within the external capsule, substantially in the space between the implant and the cylindrical electrode. The dielectric barrier formed by dielectric ring 1102 as explained above prevents generation of plasma above the ring—for example in the vicinity of insertion driver 1130.

In an exemplary embodiment wherein the internal capsule and the external capsule are made each of a polymer material with a thickness of about 1 mm, and the external diameter of the internal capsule is about 6 mm and the external diameter of the external capsule is about 10 mm, and the gaseous atmosphere inside the internal capsule and the external capsule consists of air at a reduced pressure of about 0.02 Atmospheres, a RF field at a frequency of about 1 MHz and a peak voltage between electrodes of about 5 KV is sufficient to ignite plasma in the plasma generation zone 1050.

According to some embodiments narrow bottom part 1040 of external capsule 1020 may be metallic (whereas top part 1042 is dielectric), and cylindrical electrode 1230 may contact bottom part 1040. A metallic bottom part 1040 may assist in igniting the plasma at a lower voltage, because the external capsule does not contribute to the dielectric barrier that the EM field should overcome. In some embodiments the outer surface of the internal capsule may be coated with a metallic coating for further reduction of the voltage required for plasma ignition. An electrical contact may connect cylindrical electrode 1230 to the metallic coating of the internal capsule, for example by means of a spring contact between a metallic bottom part 1040 of external capsule 1020 and the metallic coating of the internal capsule. It should be noted however that for establishing DBD operation mode of the plasma generation, the internal surface 1152 of the internal compartment 1150 of the internal capsule which faces the implant is dielectric.

According to an aspect of some embodiments, the RF signal provided to the electrode or electrodes of a portable container of the invention for plasma generation may be a continuous wave (CW) signal. According to some embodiments the RF signal provided to the electrode for applying a plasma generating field may be modulated. According to some embodiments the modulation signal may include pulse modulation. According to some embodiments, the modulation signal may include amplitude modulation. According to some embodiments the modulation signal may include a combination of types of modulation.

Figure 11:
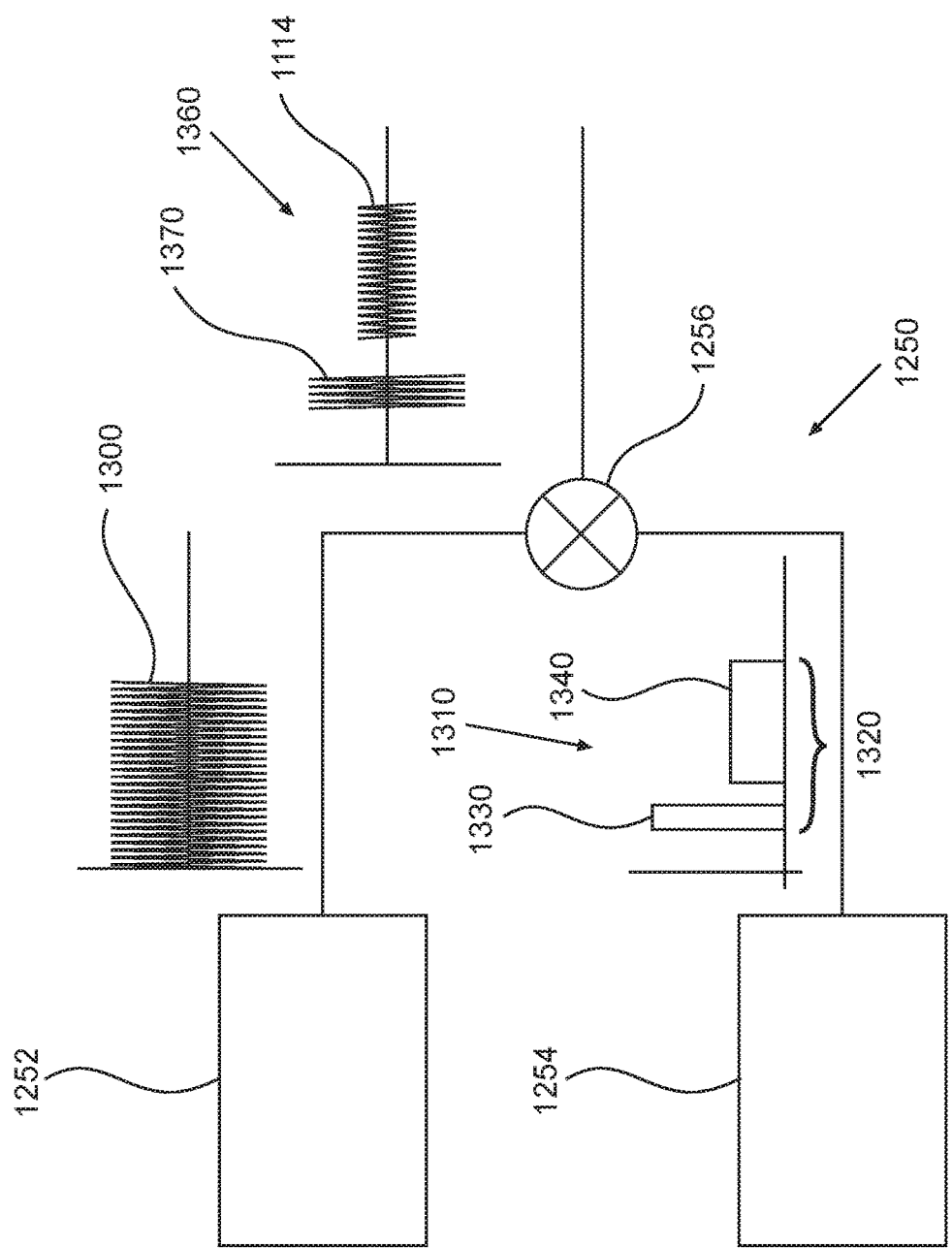
FIG. 11 schematically depicts an embodiment of an RF signal generator, configured to generate an RF signal at frequencies suitable for generating plasma in a the sealed compartment of the portable container of FIGS. 8 and 9.

FIG. 11 depicts schematically an embodiment of an RF signal generator 1250, configured to generate an RF signal at frequencies suitable for generating plasma in a sealed compartment according to the teachings herein. According to some embodiments RF signal generator 1250 may be employed as part of a power source, e.g. RF power source 1210, for generation an EM signal and an EM field suitable to excite plasma in a sealed compartment.

RF signal generator 1250 comprises an RF continuous wave (CW) source 1252 configured to generate a carrier RF signal 1300, and a pulse generator 1254 configured to generate a modulation signal 1310. RF signal generator 1250 further comprises an RF mixer 1256 functionally associated with RF CW source 1252 and with pulse generator 1254, and configured and operable to output a modulated RF signal substantially as described herein below. Carrier RF signal 1300 includes a continuous wave (CW) signal substantially at a frequency suitable for plasma generation as described above. Modulation signal 1310 comprises a repetitive pattern 1320 of pulses comprising a first modulation pulse 1330 at an amplitude A1 and pulse width PW1 between 0.5 usec (microseconds) and 15 usec, for example 5 usec, or 8 usec, or 10 usec. The first modulation pulse is followed by a second modulation pulse 1340, having an amplitude A2 smaller than A1, e.g. half of A1 or ¼ of A1. The second modulation pulse may have a pulse width PW2 greater than PW1 e.g. between 10 usec and 3000 usec, for example 120 usec. The second modulation pulse may start at time delay DT after first modulation pulse 1330 ends, where the time delay DT is shorter than an extinction time of the plasma following the end of the first modulation pulse, e.g. between 0 and 5000 usec, for example 0.4 usec.

Repetitive pattern 1320 may cyclically repeat at a pulse repetition interval (PRI) of about 2 msec. Parameters of repetitive pattern 1320, including the pulse widths values PW1 and PW2, pulse amplitudes A1 and A2, the time interval between the pulses and the PRI of repetitive pattern 1320 specified above, are provided by way of a non-limiting example, and other parameters, including other pulse widths, a different interval between the pulses, combinations of more than two pulses in a single repetitive pattern and even modulations of a carrier signal that are not purely repetitive, are all contemplated herein.

Modulation signal 1310 is mixed with carrier RF signal 1300 in RF mixer 1256 to generate a modulated RF signal 1360 having suitable frequencies and time dependency for applying a plasma-generating EM field, when supplied to an electrode or electrodes of a portable container. Modulated RF signal 1360 is generally characterized with a first relatively high amplitude and short period ignition pulse 1370, associated with first modulation pulse 1330, followed by a relatively lower amplitude, longer period work pulse 1380, associated with second modulation pulse 1340. Ignition pulse 1370 is configured to be strong enough (that is to say, of high enough intensity) to ignite plasma in an initially nonionic gas within the sealed compartment, e.g. by inducing a sufficient number of ionized atoms and molecules, and a corresponding number of free electrons, for plasma generation. Work pulse 1380 is configured to maintain the plasma generation process after plasma has been ignited by ignition pulse 1370, and may therefore have a lower amplitude than ignition pulse 1370. Maintaining the plasma generation does not necessitate work pulse 1380 to have a lower amplitude than ignition pulse 1370. However, according to some embodiments it may be advantageous to maintain a plasma generation process by applying the lowest possible EM field.

Thus, according to some embodiments it is advantageous to ignite plasma with a relatively strong ignition EM field and, subsequently, maintaining the plasma with a relatively weaker EM field. Actual power dissipation in a plasma treatment as described herein may depend on several factors, including the size (dimensions) of the implant being treated, the material from which the implant is made, the volume over which plasma is generated, and dielectric barriers within the region (such as dielectric walls of a sealed compartment or of a canister within that region). According to some embodiments a suitable surface treatment of a dental implant in the portable container 1000 in FIGS. 8, 9 and 10 may be obtained using plasma activation as described above using an RF field at a voltage of about 4 KV and consuming an average power of less than 5 W (at a duty cycle of about 10%) during a total plasma treatment time of less than 30 seconds. According to some embodiments, heat may be generated in the implant 1120 during the plasma treatment, such heat may be transferred from the implant to the outside through insertion driver 1130 and metal cap 1060 and further away from portable container, through cap electrode 1220. At an exemplary duty cycle of about 10%, RF power source 1210 in FIG. 10 may therefore be configured to provide peak power of about 50 W.

The power consumed for plasma treating as described above is largely—although not entirely—dependent on the size of the implant being treated. Thus providing satisfactory plasma treatment to a large implant such as, for example, a breast implant, may require electrical circuitry adapted for relatively high power. For example, plasma treating a breast implant may require an average power of about 100 W or 200 W and even about 500 W. The peak power may be higher accordingly—as high as 5 KW in examples discussed above—if operation scheme maintains a relatively low duty cycle of 10%. It is therefore advantageous to provide an electrical configuration which allows reducing the consumed peak power, without reducing the consumed average power, and therefore without degrading the quality of the plasma treatment nor increasing the duration thereof.

Figure 12A:
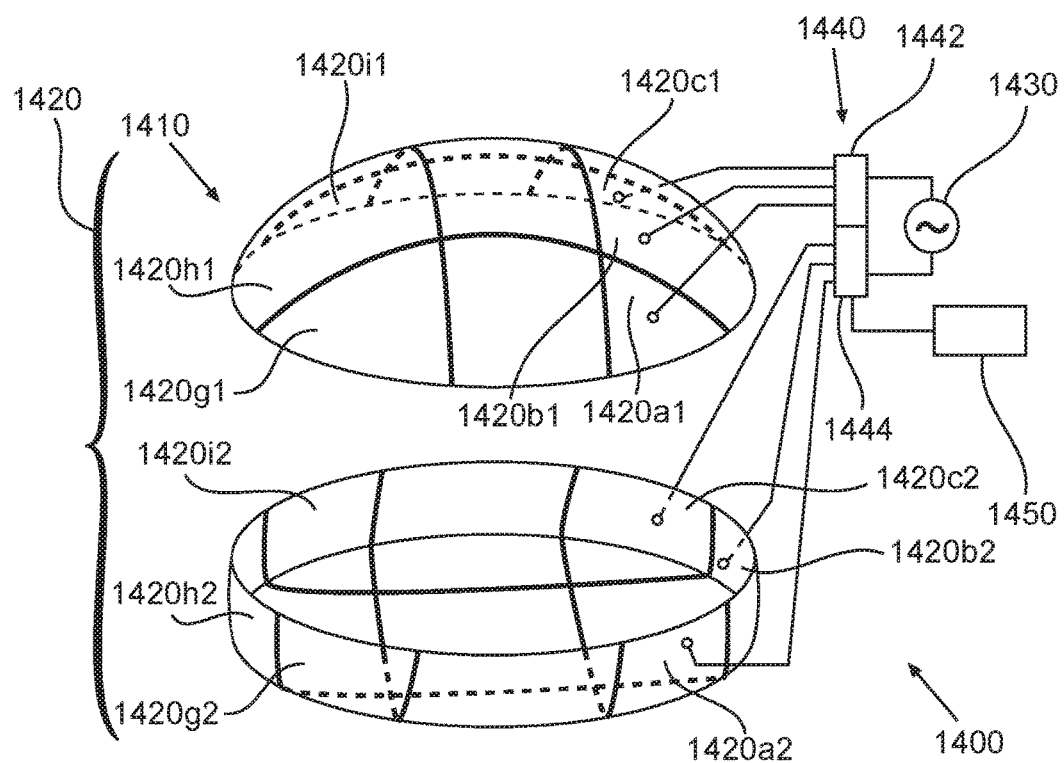
FIG. 12A schematically depicts an embodiment of an electrical configuration comprising a set of electrode pairs, suitable for plasma activation in a sealed compartment of a portable container for a breast implant, and FIG. 12B schematically depicts the electrical configuration of FIG. 12A together with the implant.
Figure 12B:
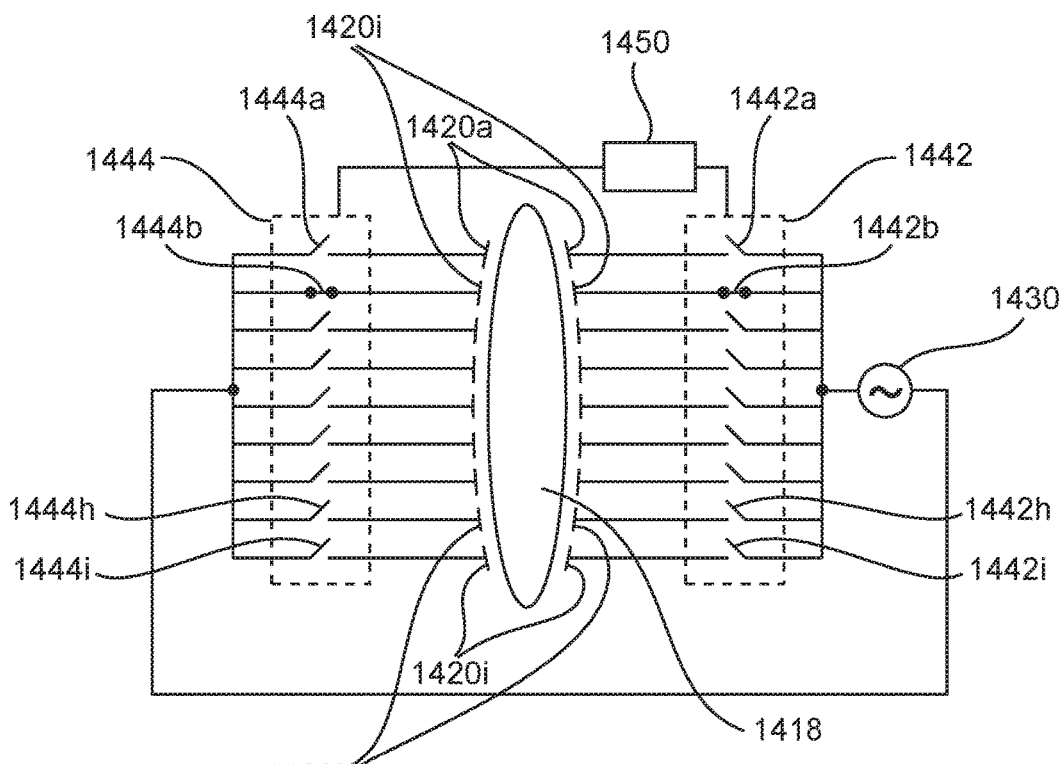

FIGS. 12A and 12B depict schematically an embodiment of an electrical configuration 1400 comprising a set 1410 of electrode pairs, suitable for plasma activation in a sealed compartment of a portable container for a breast implant 1418 (the sealed compartment, and the portable container are not shown in these Figures). Electrode pairs set 1410 comprises a multitude of pairs 1420 of electrodes—nine pairs in the exemplary, non-limiting embodiment depicted in FIGS. 12A and 12B—suitable to be used with a sealed compartment having a compartment vault with a shape of a dome and a compartment base, e.g. resembling in shape to sealed compartment 820. Each pair of electrodes 1420a, 1420b, ..., 1420i comprises a first electrode on the compartment vault and a second electrode on the compartment base. For example pair 1420a comprises a first electrode 1420a1 and a second electrode 1420a2; likewise, pair 1420b comprises a first electrode 1420b1 and a second electrode 1420b2, and so on. All the first electrodes cover together the area of the compartment vault of the sealed compartment, and all the second electrodes cover together the compartment base of the sealed compartment. Each electrode is electrically isolated from all the other electrodes in set 1410.

Electrical configuration 1400 is configured to employ electrode pairs 1420 for plasma activation sequentially, that is to say substantially a pair after a pair, as is further detailed and explained herein below, so that only a portion of the implant 1418 is plasma treated at a time. Typically, but not necessarily, the treated portion consists of two segments of the implant 1418 corresponding to a single pair of electrodes, however operation schemes wherein more than a single pair of electrodes are employed together are also contemplated. Typically, but not necessarily, the two electrodes in an electrode pair face each other separated by a portion of the implant, however operation schemes wherein a pair of electrodes consists of electrodes that do not face each other—for example electrode 1420a1 paired with electrode 1420g2—are contemplated. All the electrodes in set 1410 are dimensioned to have at least roughly a same surface area, so as to provide a similar current density when supplied with a fixed voltage, and thereby providing uniform plasma treatment over the surface of implant 1418.

Electrical configuration 1400 further comprises a RF power source 1430 configured to provide RF power for activating plasma along at least a portion of the implant. Electrical configuration 1400 further comprises a dual switch array 1440. Dual switch array 1440 comprises two switch arrays 1442 and 1444, respectively, each comprising nine electronic switches 1442a-1442i and 1444a-1444i, respectively. Each electronic switch 1442a-1442i is associated with a single first electrode 1420a1-1420i1, respectively and with RF power source 1430. Likewise, electronic switch 1444a-1444i is associated with a single first electrode 1420a2-1420i2, respectively and with RF power source 1430. Each electronic switch is configured to electrically associate or disassociate, according to a suitable command, RF power source 1430 with the respective electrode associated with the electronic switch. FIG. 12B schematically depicts electronic switches 1442b and 1444b in a closed state, thus electrically associating RF power source 1430 with electrode pair 1420b (that is to say, with electrodes 1420b1 and 1420b2), thereby enabling activating plasma in a segment of implant 1418 adjacent to electrode pair 1420b. Dual switch array 1440 is further associated with a controller 1450, optionally comprising a processor (not shown), for commanding the dual switch array.

According to some embodiments of methods of operation, RF power source may generate a constant power suitable to activate plasma between a single pair 1420x of electrodes and a corresponding segment of the implant. Only a fraction of the total peak power which is required to plasma-treat the whole implant, is required for treatment of a segment of the implant. Consequently, related circuitry, specifically RF power source 1430, may be adapted to provide a relatively low peak power, thereby relieving performance requirements, and hence reducing cost, of such circuitry.

According to some embodiments, dual switch array 1440 may be commanded to distribute RF power to the electrode pairs 1420 sequentially, namely one pair after the other. According to some embodiments, RF power source 1430 may be operated to generate RF at a fixed power level, whereas dual switch array 1440 may be employed to distribute the power to the electrode pairs, thereby providing plasma treatment to the implant segment after segment. According to some embodiments dual switch array 1440 may be commanded to associate a next pair of electrodes to RF power source 1430 before disassociating a previous pair of electrodes, thereby reducing high voltage variation in the circuitry. According to some embodiments the RF power supplied by RF power source to the electrode pairs may be modulated, e.g. as is described above in FIG. 10.

There is thus provided according to an aspect of some embodiments a portable container (10, 50, 100, 420, 520, 700, 800, 1000), for handling an implant. The portable container comprises a sealed compartment (12, 52, 102, 232, 410, 510, 720, 820, 1010) enclosing an ionisable fluid of a pre-defined composition. The sealed compartment further contains therein an implant (14, 110, 236, 416, 702, 1120, 1418) configured to be installed in a live subject. The sealed compartment is configured to be opened by a user, thereby enabling removing the implant from the portable container. The portable container comprises at least one electrode (26, 42, 60, 72, 82, 120, 130, 416 in FIG. 6A, 740, 842, 844, 1120, 1420) made of an electrical conductive material, electrically associated with an at least one electric conductor (38a, 38b, 68a, 68b, 122a, 122b, 450a, 748, 852, 854, 1060, 1442x, 1444x), outside the sealed compartment and configured for applying a plasma-generating electric field inside the sealed compartment. The portable container is thereby configured to enable storing the implant inside the sealed compartment, shipping or transporting the portable container with the implant being stored therein, and, without breaking the seal of the sealed compartment and without interfering with the pre-defined composition of the fluid, generating plasma in the fluid using an electric field, thereby surface-treating the implant.

According to some embodiments the implant is an artificial implant (14, 236, 416, 702, 1120, 1418). According to some embodiments the implant is metallic (14, 236, 416, 1120). According to some embodiments the implant is a dental implant (14, 1120). According to some embodiments the at least one electrode comprises the implant, the implant being electrically associated with the at least one conductor outside the sealed compartment (FIGS. 1A, 2A, 10).

According to some embodiments the implant (702, 1418) is dielectric at least on a surface thereof. According to some embodiments the implant is a breast implant (702). According to some embodiments the implant comprises electrically conducting parts and electrically isolating parts.

According to some embodiments the implant (110) comprises biomaterial. According to some embodiments the biomaterial is selected from the group consisting of bone graft, textile-based polymers, hernia mesh and collagen membrane. According to some embodiments the biomaterial appears in a form selected from the group consisting of powder, crushed granules, putty, chips, gel and paste.

According to some embodiments the biomaterial is disposed inside a canister (44, 44a, 44b, 44c, 44d), the canister being inside the sealed compartment and enclosing a canister fluid of a pre-defined composition. According to some embodiments the canister is sealed. According to some embodiments the canister fluid comprises a pre-defined composition of gases at a pre-defined pressure.

According to some embodiments the canister (44a, 44d) is made entirely of dielectric materials. According to some embodiments the at least one electrode (82) comprises an elongated member (88) and the canister comprises an elongated shroud (90), the elongated shroud being dimensioned to cover the electrode when the canister (44d) is inside the sealed compartment, thereby electrically isolating the electrode from the biomaterial inside the canister (44d).

According to some embodiments the canister (44b, 44c) has a metallic segment (84). According to some embodiments the metallic segment is in direct contact with the canister fluid inside the canister (44b, 44c). According to some embodiments the metallic segment is in electrical contact with the at least one electric conductor outside the sealed compartment (FIGS. 1B, 2B, 3B, 3C). According to some embodiments the metallic segment is arranged as an elongated member (86) inside the canister (44c), the biomaterial being disposed substantially around the elongated member.

According to some embodiments the fluid in the sealed compartment is a liquid. According to some embodiments the liquid comprises a saline composition. According to some embodiments the liquid comprises at least one from the group consisting of surface treatment additives, wound healing factors, bone growth factors, factor-beta, acidic fibroblast growth factors, basic fibroblast growth factors, platelet-derived growth factors and bone morphogenetic protein substances.

According to some embodiments the fluid is a gas. According to some embodiments the gas comprises at least one from the group consisting of argon, helium, nitrogen, oxygen and any combination thereof. According to some embodiments the gas has a pressure below about one atmosphere. According to some embodiments the gas has a pressure below about 10 KPa. According to some embodiments the gas has a pressure below about 2 KPa. According to some embodiments the gas has a pressure below about 1 KPa.

According to some embodiments the at least one electrode comprises only a single electrode (26, 440, 740). According to some embodiments the single electrode (26, 440) comprises an elongated conductor substantially wound around the implant. According to some embodiments the elongated conductor (440) is wound around the sealed compartment (410). According to some embodiments the portable container (10, 420) is configured for plasma generation inside the sealed compartment in an Inductive Coupled Plasma (ICP) mode of operation.

According to some embodiments the at least one electrode comprises two electrodes (26 and 42, 60 and 72, 60 and 82, 120 and 130, 842 and 844, electrode pairs 1420, respectively), electrically disconnected from one another, configured to apply a plasma generating electric field there between in a Capacitance Coupled Plasma (CPC) mode of operation. According to some embodiments at least one electrode (26, 60 120, 842 and 844, electrode pairs 1420) of the two electrodes is electrically isolated from the fluid, being thereby configured to generate plasma in the sealed compartment in a Dielectric Breakdown Discharge (DBD) mode of operation.

According to some embodiments (FIGS. 2A, 2B, 10) the plasma generating electric field may be a DC electric field. According to some embodiments (FIGS. 1A, 1B, 2A, 2B, 4, 7A, 7B, 10, 12A, 12B) the plasma generating electric field is an AC electric field. According to some embodiments the plasma generating electric field ignites the plasma at a voltage lower than 5 KV between electrodes.

According to some embodiments the sealed compartment comprises a dielectric barrier (1102) for dielectrically limiting the plasma to a plasma excitation region. According to some embodiments the dielectric barrier is configured to prevent plasma from contacting a portion of the surface of the implant.

According to some embodiments the sealed compartment comprises a sealable cover (18, 114, 722, 822, 1060) configured to cover and open an opening for implant insertion and removing into and out from the sealed compartment, the sealable opening being configured to be closed and sealed using the cover after opening.

The portable container of claim 1 wherein the sealed compartment (12) comprises a tap (48) configured to enable evacuating the sealed compartment and filling the sealed compartment with a desired fluid through the tap and further configured to be sealed after evacuating and filling.

According to some embodiments the portable container further comprises an electrical circuit electrically associated with the at least one electrode and configured to provide to the at least one electrode electric power suitable for applying a plasma generating electric field in the sealed compartment. According to some embodiments the electric circuit is configured to consume energy from a portable electric DC source, thereby being operable as a stand-alone plasma generator.

According to some embodiments the portable container (1000) further comprises an internal capsule (1100) contained within the sealed compartment (1010) and containing the implant (1120) therein. According to some embodiments the internal capsule (1100) is microbially sealed. According to some embodiments the sealed compartment (1010) is configured for freely releasing the internal capsule (1100) therefrom. According to some embodiments the electrode comprises the implant (1120), the implant being metallic, and the internal capsule (1100) comprising a metal segment (1130) being in electric contact with the metallic implant (1120) and with the at least one conductor (1060) of the portable container. According to some embodiments the implant 1120 is a dental implant.

According to some embodiments the portable container (700, 800) further comprises an external capsule (710, 810) containing therein the sealed compartment (720, 820). According to some embodiments the external capsule (710, 810) is configured for freely releasing the sealed compartment (720, 820) therefrom. According to some embodiments the at least one electrode consists of a single electrode (740) enveloping the implant (702) and electrically isolated from the fluid inside the sealed compartment. According to some embodiments the at least one electrode comprises at least one pair of electrodes (840, 1420), electrically isolated from one another and isolated from the fluid inside the sealed compartment. According to some embodiments the portable container may be dimensioned and configured to contain a breast implant (702, 1418) in the sealed compartment. According to some embodiments the portable container further comprises an implant support agent (750, 860) made of a dielectric material and disposed between the implant and a compartment internal surface (752, 862), thereby maintaining a uniform distance between the implant and the at least one electrode.

According to an aspect of some embodiments there is provided an apparatus (200, 300) for plasma treatment of an implant prior to installing the implant in a live subject. The apparatus comprises an activation device (210, 310) comprising a slot (220, 340) configured to receive a portable container (230). The portable container comprises a sealed compartment (232) enclosing an ionizable fluid of a pre-defined composition, and further contains therein an implant (236) configured to be installed in a live subject. The sealed compartment is configured to be opened by a user, thereby enabling removing the implant from the portable container. The activation device further comprises an electrical circuit (250, 350, 1200) configured to be electrically associated with at least one electrode (240a, 240b, 380). The electrical circuit is further configured to provide to the at least one electrode electric power suitable for applying a plasma generating electric field in the sealed compartment, when the portable container is disposed in the slot.

According to some embodiments the apparatus further comprises a portable container such as any portable container described herein.

According to some embodiments the electrical circuit (350, 250) is electrically associated with an electrode (380, 440 in FIG. 6A) forming a spiral, the spiral loops around the sealed compartment (232, 410) when the portable container (230, 420) is disposed in the slot (340, 220). According to some embodiments electrical circuit (250) is electrically associated with two electrodes (540 and 550, 640 and 650) being electrically disconnected from one another, each of the two electrodes forming a spiral, the two spirals are alternatingly looped around the sealed compartment (510) when the portable container (520) is disposed in the slot (250). According to some embodiments electrical circuit (1200) is electrically associated with a cylindrical electrode (1230) arranged around the sealed compartment (1010) when the portable container (1000) is disposed in the slot.

According to some embodiments the portable container (10, 50, 100, 420, 520, 700, 800, 1000) comprises at least one electrode (26, 42, 60, 72, 82, 120, 130, 416 in FIG. 6A, 740, 842, 844, 1120, 1420) made of an electrical conductive material, and configured for applying a plasma generating electric field inside the sealed compartment (12, 52, 102, 232, 410, 510, 720, 820, 1010). The electrode is associated with an electric conductor (38a, 38b, 68a, 68b, 122a, 122b, 450a, 748, 852, 854, 1060, 1442x, 1444x) outside the sealed compartment, and the apparatus comprises an electric contact (240a, 240b, 1220) electrically associated with the electric circuit and configured to electrically contact the electric conductor of the portable container when the portable container is disposed in the slot.

According to some embodiments the plasma generating electric field is a DC electric field. According to some embodiments the plasma generating electric field is an AC electric field. According to some embodiments the plasma generating electric field has a frequency above 10 KHz or between 0.1 MHz and 20 MHz, or between 20 MHz and 300 MHz or between 300 MHz and 3 GHz, or between 3 GHz and 30 GHz, or between 30 GHz and 300 GHz. According to some embodiments the plasma generating electric field has a total potential drop (e.g. between electrode 240a and electrode 240b) below 10 KV. According to some embodiments the plasma generating electric field ignites the plasma at a voltage lower than 5 KV between electrodes.

According to an aspect of some embodiments there is provided a method of handling an implant configured to be installed in a live subject. The method comprises sealing the implant in a compartment of a portable container. The compartment, when sealed with the implant therein, encloses an ionizable fluid of a pre-defined composition. The sealed compartment is configured to be opened by a user, thereby enabling removing the implant from the portable container. The portable container is configured for shipping and/or transportation with the implant being stored therein. The portable container is further configured to enable generating plasma in the fluid using an electric field, thereby surface-treating the implant, without interfering with the pre-defined composition of the fluid. The method further comprises generating plasma inside the sealed compartment by applying a plasma-generating EM field inside the sealed compartment. The method further comprises opening the sealed compartment and removing the implant therefrom.

According to some embodiments the method further comprises installing the implant in a live subject. According to some embodiments the step of generating plasma and the step of installing the implant are carried out substantially at a same medical treatment site. According to some embodiments the method further comprises, following the step of sealing the implant in the compartment of the portable container, transporting the portable container to the medical treatment site.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A portable container for handling an implant, the portable container comprising:

a sealed compartment enclosing an ionizable fluid of a pre-defined composition, said sealed compartment further containing an implant therein configured to be installed in a live subject, said sealed compartment configured to be opened by a user to thereby enable removing said implant from said portable container; and at least one electrode made of an electrical conductive material, electrically associated with an at least one electric conductor outside said sealed compartment, and configured for applying a plasma-generating electric field inside said sealed compartment, wherein the portable container is configured to enable storing said implant inside said sealed compartment, shipping said portable container with said implant being stored therein, and, without breaking the seal of the sealed compartment, generating plasma in said fluid using an electric field, thereby surface-treating said implant.

2. The portable container of claim 1 wherein said implant includes an artificial implant.

3. The portable container of claim 2 wherein said implant is metallic.

4. The portable container of claim 3 wherein said at least one electrode comprises said implant, said implant being electrically associated with said at least one conductor outside said sealed compartment.

5. The portable container of claim 4 wherein the implant is electrically connected with the at least one conductor outside the sealed compartment.

6. The portable container of claim 4 wherein the implant is capacitively coupled with the at least one conductor outside the sealed compartment.

7. The portable container of claim 2 wherein said implant is dielectric at least on a surface thereof.

8. The portable container of claim 7 wherein said implant includes a breast implant.

9. The portable container of claim 2 wherein said implant includes electrically conducting parts and electrically isolating parts.

10. The portable container of claim 2 wherein said implant includes biomaterial.

11. The portable container of claim 10 wherein said biomaterial includes one or more of bone graft, hydroxyapatite, textile-based polymers, a hernia mesh, or a collagen membrane.

12. The portable container of claim 11 wherein said at least one electrode includes an elongated electrically conducting rod extending inside said sealed compartment and having an electrical contact with said at least one electric conductor outside said sealed compartment, said biomaterial in a form selected from the group consisting of powder, crushed granules, putty, chips, gel, paste, and any combination thereof, said biomaterial disposed inside said sealed compartment around said elongated electrically conducting rod.

13. The portable container of claim 1 wherein said fluid includes a gas including at least one gas selected from the group consisting of argon, helium, nitrogen, oxygen, and any combination thereof.

14. The portable container of claim 13 wherein said gas has a pressure below about 10 KPa.

15. The portable container of claim 1 wherein said at least one electrode includes only a single electrode.

16. The portable container of claim 1 wherein said at least one electrode includes two electrodes, electrically disconnected from one another, configured to apply a plasma-generating electric field therebetween in a Capacitance Coupled Plasma (CPC) mode of operation.

17. The portable container of claim 1 wherein said at least one electrode is electrically isolated from said fluid, being thereby configured to generate plasma in said sealed compartment in a Dielectric Breakdown Discharge (DBD) mode of operation.

18. The portable container of claim 1, further comprising an external capsule containing therein said sealed compartment.

19. The portable container of claim 18 wherein said external capsule is configured for freely releasing said sealed compartment therefrom.

20. The portable container of claim 18 wherein said implant includes a dental implant, and wherein said at least one electrode comprises said implant, said implant being electrically connected with said at least one conductor outside said sealed compartment.

21. An apparatus for plasma treatment of an implant prior to installing said implant in a live subject, the apparatus comprising:

the portable container of claim 1 and an activation device including:

a slot configured to receive a portable container detachable from said activation device, said portable container including a sealed compartment enclosing an ionizable fluid of a pre-defined composition, said sealed compartment further containing an implant therein configured to be installed in a live subject, said sealed compartment configured to be opened by a user to thereby enable removing said implant from said portable container; and an electrical circuit configured to be electrically associated with at least one electrode and configured to provide to said at least one electrode electric power suitable for applying a plasma generating electric field in said sealed compartment, when said portable container is disposed in said slot.

22. A method of handling an implant configured to be installed in a live subject, the method comprising:

generating plasma inside a sealed compartment of a portable container by applying a plasma-generating electromagnetic (EM) field inside the sealed compartment, the sealed compartment enclosing an ionizable fluid of a pre-defined composition and having the implant sealed therein, said plasma being generated without breaking the seal of the sealed compartment, following shipping the portable container with the implant being stored therein, wherein the sealed compartment is configured to be opened by a user to thereby enable removing the implant from the portable container; and following said generating plasma, opening the sealed compartment and removing the implant therefrom.

23. The method of claim 22, further comprising installing the implant in a live subject.

24. The method of claim 22 wherein said generating plasma is done by disposing the portable container in a slot of an activation device, the activation device having an electrical circuit configured to be electrically associated with at least one electrode and configured to provide to the at least one electrode electric power suitable for applying a plasma generating electric field in the sealed compartment, when the portable container is disposed in the slot.

25. The method of claim 22:

wherein the portable container includes an external capsule encapsulating therein the sealed compartment; and further comprising releasing the sealed compartment from the external capsule, after said generating plasma and prior to said opening the sealed compartment.

26. The method of claim 24 wherein said at least one electrode is electrically isolated from said fluid, being thereby configured to generate plasma in said sealed compartment in a Dielectric Breakdown Discharge (DBD) mode of operation.

27. The method of claim 23 wherein a time period between sealing the implant in the sealed compartment and removing the implant therefrom after plasma treatment, is at least two days.

28. The method of claim 23 wherein the implant is taken to surgery immediately following said removing the implant from the sealed compartment.

* * * * *